US010570371B2

(12) United States Patent
Kwon et al.

(10) Patent No.: US 10,570,371 B2
(45) **Date of Patent: *Feb. 25, 2020**

(54) METHODS FOR ISOLATING AND PROLIFERATING AUTOLOGOUS CANCER ANTIGEN-SPECIFIC CD8+T CELLS

(71) Applicant: Eutilex Co., Ltd., Seoul (KR)

(72) Inventors: Byoung S. Kwon, Gwangmyeong-si (KR); Hyun-Guy Kang, Seoul (KR); Kwang-Hui Kim, Gyeonggi-do (KR); Young-Woo Kim, Gyeonggi-do (KR); Young Ho Kim, Goyang-si (KR); Byung-Kiu Park, Seoul (KR); Sang-Yoon Park, Seoul (KR); Sang-Jae Park, Gyeonggi-do (KR); Hyeon-Seok Eom, Seoul (KR); Ho-Sik Oh, Goyang-si (KR); Heon Yoo, Seoul (KR); Don-Gil Lee, Gyeonggi-do (KR); Seung-Hoon Lee, Seoul (KR); Young-Joo Lee, Seoul (KR); Jin-Soo Lee, Gyeonggi-do (KR); Beom-Kyu Choi, Gyeonggi-do (KR)

(73) Assignee: Eutilex Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/936,209

(22) Filed: Mar. 26, 2018

(65) Prior Publication Data

US 2018/0216066 A1 Aug. 2, 2018

Related U.S. Application Data

(63) Continuation of application No. 15/691,179, filed on Aug. 30, 2017, which is a continuation of application No. 14/656,355, filed on Mar. 12, 2015, now abandoned.

(30) Foreign Application Priority Data

Mar. 12, 2014 (KR) ........................ 10-2014-0029198

(51) Int. Cl.

*C12N 5/0783* (2010.01)
*C12N 5/0789* (2010.01)

(52) U.S. Cl.

CPC ......... *C12N 5/0636* (2013.01); *C12N 5/0647* (2013.01); *C12N 2501/2302* (2013.01); *C12N 2501/50* (2013.01); *C12N 2501/52* (2013.01); *C12N 2501/998* (2013.01)

(58) Field of Classification Search

CPC ........................... C12N 5/0647; C12N 5/0636
See application file for complete search history.

(56) References Cited

U.S. PATENT DOCUMENTS

| | | | |
|---|---|---|---|
| 6,458,934 B1 | 10/2002 | Hong et al. | |
| 6,905,685 B2 | 6/2005 | Kwon | |
| 7,932,045 B2 | 4/2011 | Kwon | |
| 2004/0224402 A1 | 11/2004 | Bonyhadi et al. | |
| 2006/0106196 A1* | 5/2006 | Gaudernack | A61K 38/45 530/326 |
| 2008/0261307 A1 | 10/2008 | Kwon et al. | |
| 2010/0158931 A1* | 6/2010 | Weinschenk | A61K 39/0011 424/185.1 |
| 2014/0377255 A1 | 12/2014 | Ahrens et al. | |
| 2015/0259646 A1 | 9/2015 | Kwon et al. | |
| 2016/0244528 A1 | 8/2016 | Gray | |
| 2018/0057793 A1 | 3/2018 | Kwon et al. | |

FOREIGN PATENT DOCUMENTS

| | | |
|---|---|---|
| JP | H10-507627 A | 7/1998 |
| JP | 2002-531383 | 9/2002 |
| JP | 2009-536036 A | 10/2009 |
| JP | 2007-532095 | 11/2019 |
| KR | 2004/0083918 | 10/2004 |
| KR | 100468321 | 1/2005 |
| KR | 100500283 | 7/2005 |

(Continued)

OTHER PUBLICATIONS

Jager et al (Journal of Experimental Medicine, 1998, vol. 187, pp. 265-270) (Year: 1998).*

Tsuboi et al (Cancer Immunology Immunotherapy, 2002, vol. 51, pp. 614-620) (Year: 2002).*

Cheever et al, Clinical Cancer Research, 2009, vol. 15, pp. 5323-5337 (Year: 2009).*

Hochst and Diehl, Oncoimmunology, 2012, vol. 1, pp. 1620-1622 (Year: 2012).*

The abstract of Nakamura et al (Blood, 2011, vol. 118, No. 21, pp. 435-436) (Year: 2011).*

The abstract of Doering et al (Journal of Immunotherapy, 2011, vol. 34, No. 9, pp. 689-690) (Year: 2011).*

Yee et al (Journal of Immunology, 1999, vol. 162, pp. 2227-2234) (Year: 1999).*

(Continued)

*Primary Examiner* — Karen A. Canella

(74) *Attorney, Agent, or Firm* — Fish & Richardson P.C.

(57) ABSTRACT

Provided is a method for isolating and proliferating autologous cancer antigen-specific $CD8^+$ T cells, and more particularly, a method for selecting an epitope recognized by $CD8^+$ T cells from autologous cancer antigens present in blood of individual cancer patients; and isolating autologous cancer antigen-specific $CD8^+$ T cells by using a peptide of the selected epitope, and a method of massively proliferating $CD8^+$ T cells by using the method. According to the present invention, it is possible to isolate autologous cancer antigen-specific $CD8^+$ T cells by using the peptide of the CD8 T cell epitope of the autologous cancer antigen present in blood of individual cancer patients instead of a heterologous antigen. Therefore, by using T cells recognizing the autologous cancer antigen, it is possible to effectively select and eliminate cancer cells derived from the cancer patient's own cells. Thus, T cells can be applied to treatment and alleviation of cancer diseases without side effects.

15 Claims, 17 Drawing Sheets

Specification includes a Sequence Listing.

(56) References Cited

FOREIGN PATENT DOCUMENTS

| | | | |
|---|---|---|---|
| KR | 2008-0084308 | A | 9/2008 |
| KR | 10-0882445 | B1 | 2/2009 |
| KR | 100882445 | | 2/2009 |
| KR | 2010-0011821 | A | 2/2010 |
| KR | 2010-0043130 | A | 4/2010 |
| KR | 10-1103603 | B1 | 1/2012 |
| KR | 101503341 | | 3/2015 |
| KR | 10-2016-0165224 | | 12/2016 |
| RU | 2551963 | | 10/2015 |
| WO | WO-96/06929 | A2 | 3/1996 |
| WO | WO-01/36452 | A2 | 5/2001 |
| WO | WO-2001/042270 | A1 | 6/2001 |
| WO | WO-2002/072013 | A2 | 9/2002 |
| WO | WO-03/049755 | A1 | 6/2003 |
| WO | WO-2004/016734 | A2 | 2/2004 |
| WO | WO 2005/035584 | | 4/2005 |
| WO | WO 2006/126835 | | 11/2006 |
| WO | WO-2007/131210 | A2 | 11/2007 |
| WO | WO 2012/032433 | | 3/2012 |
| WO | WO 2016/029073 | | 2/2015 |
| WO | WO 2016/119923 | | 8/2015 |
| WO | WO 2015/179236 | | 11/2015 |
| WO | WO 2016/205277 | | 12/2016 |

OTHER PUBLICATIONS

Parkhurst et al, Cancer Research, 1998, vol. 58, pp. 4895-4901 (Year: 1998).*

Oji et al (Japanese Journal of Cancer Research, Feb. 1999, vol. 90, pp. 194-204) (Year: 1999).*

Chen et al (Journal of Immunology, 2000, vol. 165, pp. 948-955) (Year: 2000).*

Miyagawa et al (Oncology, 2006, vol. 70, pp. 54-62) (Year: 2006).*

Bhasin, M. and Raghava, G.P., Prediction of CTL epitopes using QM, SVM and ANN techniques, Vaccine, 22(23-24):3195-3201 (2004).

Call, K.M. et al., Isolation and characterization of a zinc finger polypeptide gene at the human chromosome 11 Wilms' tumor locus, Cell, 60(3):509-520 (1990).

Choi, B. K. et al., 4-1BB-based isolation and expansion of CD8+ T cells specific for self-tumor and non-self-tumor antigens for adoptive T-cell therapy, J Immunother, 37(4):225-236 (2014).

Decoster, L. et al., Vaccination therapy for non-small-cell lung cancer: review of agents in phase III development, Annals of Oncology, 23(5):1387-1393 (2012).

GenBank AA061088.1, 2 pages, downloaded from NCBI on Jul. 11, 2016.

Gnjatic, S. et al., NY-ESO-1: review of an immunogenic tumor antigen, Adv Cancer Res., 95:1-30 (2006).

International Search Report for PCT/KR2015/0002356, ISA/KR, 8 pages (dated Jul. 10, 2015). English Translation.

Jager et al., Simultaneous Humoral and Cellular Immune Response against Cancer-Testis Antigen NY-ESO-1: Definition of human Histocompatibility Leukocyte Antigen (HLA)-A2-binding Peptide Epitopes, Journal of Experimental Medicine, 187: 265-270 (1998).

Kim, N.W. et al., Specific association of human telomerase activity with immortal cells and cancer, Science, 266(5193):2011-2015 (1994).

Larsen, M.V. et al., Large-scale validation of methods for cytotoxic T-lymphocyte epitope prediction, BMC Bioinformatics, 8:424 (2007).

Nakahara, Y. et al., Expression of the Wilms' tumor gene product WT1 in glioblastomas and medulloblastomas, Brian Tumor Pathology, 21(3):113-116 (2004).

Ramakrishnan, S. et al., Expression Profile of the Putative Catalytic Subunit of the Telomerase Gene, Cancer Research, 58:622-625 (1998).

Rammensee, H.-G., et al., SYFPEITHI: database for MHC ligands and peptide motifs, Immunogenetics, 50:213-219 (1999).

Richards, D. F. et al, Glucocorticoids drive human CDb+ T cell differentiation towards a phenotype with high IL-10 and reduced IL-4, IL-5 and IL-13 production, Eur. J. Immunol. 30:2344-2354 (2000).

Scanlan, M.J. et al., Cancer/testis antigens: an expanding family of targets for cancer immunotherapy, Immunol Rev., 188:22-32 (2002).

Tsuboi, A. et al., Enhanced induction of human WT1-specific cytotoxic T lymphocytes with a 9-mer WT1 peptide modified at HLA-A*2402-binding residues, Cancer Immunol Immunother, 51: 614-620 (2002).

Written Opinion for PCT/KR2015/0002356, ISA/KR, 9 pages (dated Jul. 10, 2015). English Translation.

Yee, C., Adoptive T Cell Therapy for Cancer: Boutique Therapy or Treatment Modality?, Clin Cancer Res., 19(17):4550-4553 (2013).

Barbas et al., Combinatorial Immunoglobulin Libraries on the Surface of Phage (Phabs): Rapid Selection of Antigen-Specific Fabs, Methods: A Companion to Methods in Enzymology, 2(2): 119-124 (1991).

Bartkowiak, T. and M. Curran, 4-1 BB agonists: multi-potent potentiators of tumor immunity, Frontiers in Oncology, 5(117): 1-16 (2015).

Chen et al., Combination of 4-1 BB Agonist and PD-1 Antagonist Promotes Antitumor Effector/Memory CDS T Cells in a Poorly Immunogenic Tumor Model, Cancer Immunology Research, 3(2): 149-160 (2015).

Fisher et al, "Targeting of 4-1 BB by monoclonal antibody PF-05082566 enhances Tcell function and promotes anti-tumor activity," Cancer Immunology, Immunotherapy, 61(10): 1721-1733 (2012).

Garn I-Wagner et al., 4-1 BB Is Expressed on CD45RAhiROhi Transitional T Cell in Humans, Cellular Immunology, 169: 91-98 (1996).

Hinrichs & Restifo, Reassessing target antigens for adoptive T cell therapy Nature Biotechnol., Nov. 13, 2013, 31:999-1008.

International Search Report for PCT/IB2018/000043, ISA/AU, 5 pages (dated May 16, 2018).

Kim et al, Combination Therapy with Cisplatin and Anti-4-1 BB: Synergistic Anticancer Effects and Amelioration of Cisplatin-Induced Nephrotoxicity, Cancer Res., 68: 7264-7269 (2008).

Kim et al., Human 4-1 BB regulates CD28 co-stimulation to promote Thi cell responses, Eur. J. Immunol., 28: 991-890 (1998).

Kim et al., Neutralizing human monoclonal antibodies to hepatitis A virus recovered by phage display, Virology, 318: 598-607 (2004).

Kim et al., Selection of an affinity-matured antibody against a defined epitope by phage display of an immune antibody library, Journal of Immunological Methods, 329: 176-183 (2008).

Kwon et al., cDNA sequences of two inducible T-cell genes, Proc. Natl. Acad. Sci. USA, 86: 1963-1967 (1989).

Kwon et al., Isolation and initial characterization of multiple species of T-lymphocyte subset cDNA clones, Proc. Natl. Acad. Sci. USA, 84: 2896-2900 (1987).

Lee et al., Molecular cloning of agonistic and antagonistic monoclonal antibodies against human 4-1 BB, Eur. J. Immunogenetics, 29: 449-452 (2002).

Lynch, D.H., The promise of 4-1 BB (CD137)-mediated immunomodulation and the immunotherapy of cancer, Immunol. Rev., 222:277-86 (2008).

Richards et al, "Glucocorticoids drive human CD8 T cell differentiation towards a phenotype with high IL-10 and reduced IL-4, IL-5 and IL-13 production," Eur J Immunol., Aug. 2000, 30:2344-2354.

Shindo, Y. et al., Combination Immunotherapy with 4-1 BB Activation and PD-1 Blockade Enhances Antitumor Efficacy in a Mouse Model of Subcutaneous Tumor, Anticancer Research, 35: 129-136 (2015).

Son et al., Humanization of agonistic anti-human 4-1 BB monoclonal antibody using a phagedisplayed combinatorial library, Journal of Immunological Methods, 286: 187-201 (2004).

Taylor, S.F. and Bender, B.S., Beta 2-microglobulin-deficient mice demonstrate class II MHC restricted anti-viral CD4+ but not CDS+ CTL against influenza-sensitized autologous splenocytes, Immunol. Lett., 46(1-2): 67-73 (1995).

Vinay, D. S. et al, Dual immunoregulatory pathways of 4-1 BB signaling, J. Mol. Med. ( Berl), 84(9): 726-36 (2006).

(56) References Cited

OTHER PUBLICATIONS

Vinay, D.S. and Kwon, B.S., 4-1 BB (CD137), an inducible costimulatory receptor, as a specific target for cancer therapy, BMB Rep. 4 7(3): 222-9 (2014).
Walter et al, "Multipeptide immune response to cancer vaccine IMA901 after single-dose cyclophosphamide associates with longer patient survival," Nature Med., Aug. 2012, 18:1254-1261.
Wölff et al., "Use of CD137 to Study the Full Repertoire of CD8+ T Cells Without the Need to Know Epitope Specificities," Cytometry A, Nov. 2008, 73:1043-1049.
Written Opinion for PCT/IB2018/000043, ISA/AU, 5 pages (dated May 16, 2018).
Zhou et al., Characterization of human homologue of 4-1 BB and its ligand, Immunology Letters, 45: 67-73 (1995).
Croft, M., "The role of TNF superfamily members in T-cell function and diseases," Nat. Rev. Immunol., 2009, 9(4): 271-85.
European Search Report in Application No. 18736336, dated Sep. 11, 2019, 9 pages.
Li et al., "Immunotherapy of melanoma with the immune costimulatory monoclonal antibodies targeting CD137", Clinical Pharmacology: Advances and Applications, p. 47, 2013.
Japanese Office Action in Application No. 2019-517981, dated Oct. 10, 2019 English Translation, 2 pages.
Murillo et al., "Therapeutic Antitumor Efficacy of Anti-CD137 Agonistic Monoclonal Antibody in Mouse Models of Myeloma", Clin Cancer Res., 14(21), 6895-6906, 2008.
Russian Office Action in Application No. 2019116731, dated Nov. 12, 2019, 4 pages.

* cited by examiner

Figure 3:
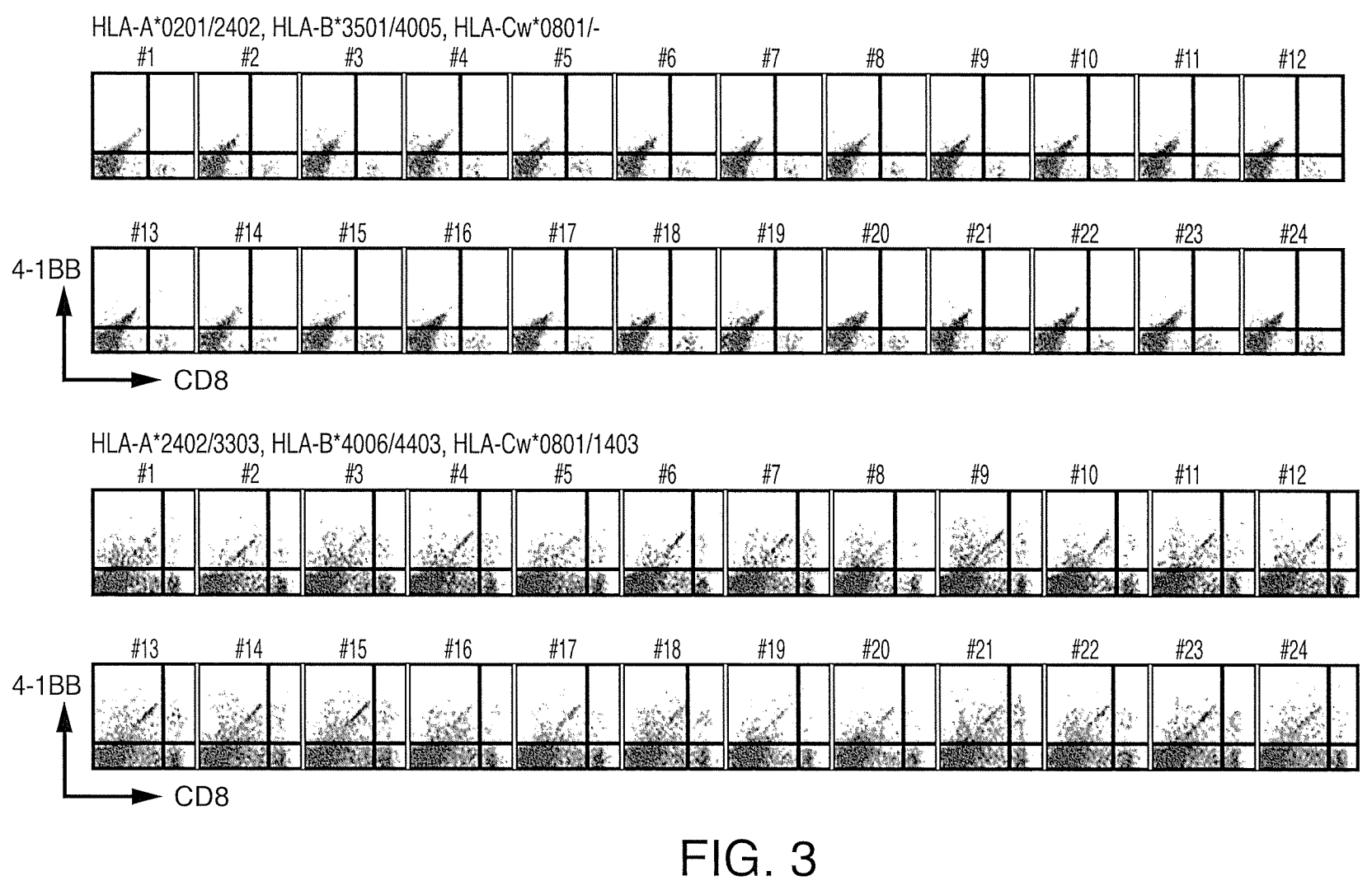

HLA-A*0201/2402, HLA-B*3501/4005, HLA-Cw*0801/-

1 #2 #3 #4 #5 #6 #7 #8 #9 #10 #11 #12

13 #14 #15 #16 #17 #18 #19 #20 #21 #22 #23 #24

4-1BB

CD8

HLA-A*2402/3303, HLA-B*4006/4403, HLA-Cw*0801/1403

SEQUENCE LISTING

<160> NUMBER OF SEQ ID NOS: 102

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic epitope of hTERT

<400> SEQUENCE: 1

```
Cys Leu Lys Glu Leu Val Ala Arg Val
1               5
```

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic epitope of hTERT

<400> SEQUENCE: 2

```
Pro Leu Phe Leu Glu Leu Leu
1               5
```

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic epitope of hTERT

<400> SEQUENCE: 3

```
Ala Ala Val Thr Pro Ala Ala
1               5
```

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic epitope of WT1

<400> SEQUENCE: 4

```
Ser Leu Gly Glu Gln Gln Val Ser Val
1               5
```

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic epitope of WT1

<400> SEQUENCE: 5

```
Arg Met Phe Pro Asn Ala Pro Val Leu
1               5
```

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic epitope of WT1

<400> SEQUENCE: 6

Cys Met Thr Trp Asn Gln Met Asn Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic epitope of WT1

<400> SEQUENCE: 7

Val Leu Asp Phe Ala Pro Pro Gly Ala
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic epitope of NY ESO1

<400> SEQUENCE: 8

Ser Ile Ser Ser Cys Leu Gln Gln Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic epitope of NY ESO1

<400> SEQUENCE: 9

Arg Leu Leu Glu Phe Tyr Leu Ala Met
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic epitope of NY ESO1

<400> SEQUENCE: 10

Gly Val Leu Leu Lys Glu Phe Thr Val
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic epitope of NY ESO1

<400> SEQUENCE: 11

Ile Leu Thr Ile Arg Leu Thr Ala Ala
1               5

<210> SEQ ID NO 12

<211> LENGTH: 9
<212> TYPE: PRT
<213> ORGANISM: Artificial Sequence
<220> FEATURE:
<223> OTHER INFORMATION: Description of Artificial Sequence: Synthetic epitope of MAGE A3

<400> SEQUENCE: 12

Leu Leu Ile Ile Val Leu Ala Ile Ile
1 5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic epitope of MAGE A3

<400> SEQUENCE: 13

Lys Ile Trp Glu Glu Leu Ser Val Leu
1 5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic epitope of MAGE A3

<400> SEQUENCE: 14

Leu Val Phe Gly Ile Glu Leu Met Glu Val
1 5 10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic epitope of MAGE A3

<400> SEQUENCE: 15

Ser Leu Pro Thr Thr Met Asn Tyr Pro Leu
1 5 10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Ala Ala Phe Arg Ala Leu Val Ala Gln Cys Leu
1 5 10

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

```
Leu Ala Phe Gly Phe Ala Leu Leu
1               5


<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Gly Asp Asp Val Leu Val His
1               5


<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Val Leu Val Ala Pro Ser Cys Ala
1               5


<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ala Ala Thr Gln Ala Arg Pro
1               5


<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Gly Thr Arg His Ser His
1               5


<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Glu Gln Leu Arg Pro Ser Phe Leu Leu Ser Ser Leu Arg Pro Ser
1               5                   10                  15

Leu


<210> SEQ ID NO 23
<211> LENGTH: 7
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 23

Gln Ser Ile Gly Ile Arg Gln
1 5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Ile Val Asn Met Asp Tyr Val
1 5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Arg Pro Gly Leu Leu Gly Ala Ser Val
1 5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Thr Leu Thr Asp Leu Gln Pro
1 5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Leu Leu Cys Ser Leu Cys Tyr Gly
1 5

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Leu Val Arg Gly Val Pro Glu Tyr Gly Cys Val Val Asn Leu Arg
1 5 10 15

```
<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Ser Ser Tyr Ala Arg Thr Ser Ile Arg Ala Ser Leu
1               5                   10


<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Tyr Lys Ile Leu Leu Leu Gln Ala Tyr
1               5                   10


<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Gly Ala Lys Gly Ala Ala
1               5


<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Val Pro Leu Leu Gly Ser Leu
1               5


<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Thr Gln Leu Ser Arg Lys Leu Pro
1               5


<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 34

Ala Leu Glu Ala Ala Ala Asn Pro Ala Leu
1 5 10

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Ile Leu Ala Lys Phe Leu His Trp Leu
1 5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Arg Leu Val Asp Asp Phe Leu Leu Val
1 5

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Glu Ala Arg Pro Ala Leu Leu Thr Ser Arg Leu Arg Phe Ile Pro Lys
1 5 10 15

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Arg Leu Phe Phe Tyr Arg Lys Ser Val
1 5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Tyr Leu Phe Phe Tyr Arg Lys Ser Val
1 5

<210> SEQ ID NO 40
<211> LENGTH: 10

<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Asp Leu Gln Val Asn Ser Leu Gln Thr Val
1 5 10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Tyr Leu Gln Val Asn Ser Leu Gln Thr Val
1 5 10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Gly Leu Leu Gly Ala Ser Val Leu Gly Leu
1 5 10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Ala Leu Leu Thr Ser Arg Leu Arg Phe Ile
1 5 10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Arg Leu Thr Ser Arg Val Lys Ala Leu
1 5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Thr Tyr Val Pro Leu Leu Gly Ser Leu 1 5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Cys Tyr Gly Asp Met Glu Asn Lys Leu
1 5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Ala Tyr Gln Val Cys Gly Pro Pro
1 5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Val Tyr Gly Phe Val Arg Ala Cys Leu
1 5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Val Tyr Ala Glu Thr Lys His Phe Leu
1 5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Asp Tyr Val Val Gly Ala Arg Thr Phe
1 5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic

```
      peptide

<400> SEQUENCE: 51

Ala Leu Leu Pro Ala Val Pro Ser Leu
1               5


<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Leu Asn Ala Leu Leu Pro Ala Val
1               5


<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Leu Gly Glu Gln Gln Tyr Ser Val
1               5


<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Met Phe Pro Asn Ala Pro Tyr Leu
1               5


<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Val Phe Arg Gly Ile Gln Asp Val
1               5


<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Gly Gln Phe Thr Gly Thr Ala Gly Ala
1               5                   10


<210> SEQ ID NO 57
```

<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Ala Pro Gly Cys Asn Lys Arg Tyr Phe
1 5

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Gln Tyr Arg Ile His Thr His Gly Val Phe
1 5 10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Ala Phe Thr Val His Phe Ser Gly Gln Phe
1 5 10

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Arg Trp Pro Ser Cys Gln Lys Lys Phe
1 5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Arg Val Pro Gly Val Ala Pro Thr Leu
1 5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Asp Phe Lys Asp Cys Glu Arg Arg Phe
1 5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Arg Thr Pro Tyr Ser Ser Asp Asn Leu
1 5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Thr Ser Glu Lys Pro Phe Ser Cys Arg
1 5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Phe Ser Arg Ser Asp Gln Leu Lys Arg
1 5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Leu Ser His Leu Gln Met His Ser Arg
1 5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Ser Leu Ala Gln Asp Ala Pro Pro Leu
1 5

<210> SEQ ID NO 68
<211> LENGTH: 10
<212> TYPE: PRT
<213> ORGANISM: Artificial Sequence
<220> FEATURE:

<223> OTHER INFORMATION: Description of Artificial Sequence: Synthetic peptide

<400> SEQUENCE: 68

Leu Leu Met Trp Ile Thr Gln Cys Phe Leu
1 5 10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Asp Ala Pro Pro Leu Pro Val Pro Gly Val
1 5 10

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Thr Val Ser Gly Asn Ile Leu Thr Ile
1 5

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Gln Leu Gln Leu Ser Ile Ser Ser Cys Leu
1 5 10

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Ser Leu Leu Met Trp Ile Thr Gln Cys
1 5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Glu Phe Thr Val Ser Gly Asn Ile Leu
1 5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Ser Gly Leu Asn Gly Cys Cys Arg
1 5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Ser Ser Cys Leu Gln Gln Leu Ser Leu
1 5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Phe Ala Thr Pro Met Glu Ala Glu Leu
1 5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Ile Thr Gln Cys Phe Leu Pro Val Phe
1 5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

Leu Thr Ala Ala Asp His Arg Gln Leu
1 5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 79

Tyr Leu Ala Met Pro Phe Ala Thr Pro Met
1 5 10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

Ala Thr Pro Met Glu Ala Glu Leu Ala Arg
1 5 10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Ala Ser Gly Pro Gly Gly Gly Ala Pro Arg
1 5 10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Pro Val Pro Gly Val Leu Leu Lys Glu Phe
1 5 10

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Ala Leu Ser Arg Lys Val Ala Glu Leu
1 5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Gly Leu Leu Ile Ile Val Leu Ala Ile
1 5

<210> SEQ ID NO 85
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 85

Ile Leu Gly Asp Pro Lys Lys Leu Leu
1               5


<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Leu Val Glu Val Thr Leu Gly Glu Val
1               5                   10


<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Leu Val Glu Thr Ser Tyr Val Lys Val
1               5                   10


<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Ala Leu Ser Arg Lys Val Ala Glu Leu
1               5                   10


<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Tyr Pro Pro Leu His Glu Trp Val Leu
1               5                   10


<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Tyr Ile Phe Ala Thr Cys Leu Gly Leu
1               5
```

```
<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Val Phe Glu Gly Arg Glu Asp Ser Ile Leu
1               5                   10


<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu Gly Leu Glu Ala Arg Gly Glu Ala Leu
1               5                   10


<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Phe Pro Asp Leu Glu Ser Glu Phe
1               5


<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Glu Phe Leu Trp Gly Pro Arg Ala Leu
1               5


<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Val Ala Glu Leu Val His Phe Leu Leu
1               5


<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 96

Ile Phe Ser Lys Ala Ser Ser Ser Leu
1 5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

Lys Val Leu His His Met Val Lys Ile
1 5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 98

Val Asp Pro Ile Gly His Leu Tyr Ile
1 5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Ile Met Pro Lys Ala Gly Leu Leu Ile
1 5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Ser Ile Leu Gly Asp Pro Lys Lys Leu
1 5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Val Lys Ile Ser Gly Gly Pro His Ile
1 5

<210> SEQ ID NO 102
<211> LENGTH: 9
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 102

Leu Gly Leu Ser Tyr Asp Gly Leu Leu
1               5
```

METHODS FOR ISOLATING AND PROLIFERATING AUTOLOGOUS CANCER ANTIGEN-SPECIFIC CD8+T CELLS

CROSS-REFERENCE TO RELATED APPLICATIONS

This application is a continuation of U.S. patent application Ser. No. 15/691,179, filed on Aug. 30, 2017, which is a continuation of U.S. patent application Ser. No. 14/656,355, filed Mar. 12, 2015, which claims priority under 35 U.S.C. § 119 of Korean Patent Application No. 10-2014-0029198, filed on Mar. 12, 2014, the entire contents of each of which are hereby incorporated by reference in their entirety.

STATEMENT REGARDING SEQUENCE LISTING

The Sequence Listing associated with this application is provided in text form in lieu of a paper copy, and is hereby incorporated by reference into the specification. The name of the text file containing the Sequence Listing is 2012994-0037_SL.txt. The text file is 23,877 bytes, was created on Oct. 31, 2018, and is being submitted electronically via EFS-Web, concurrent with the filing of the specification.

BACKGROUND OF THE INVENTION

The present invention relates to a method for isolating and proliferating autologous cancer antigen-specific CD8$^+$ T cells. More particularly, the present invention relates to a method for selecting an epitope recognized by CD8$^+$ T cells from autologous cancer antigens present in blood of individual cancer patients; and isolating autologous cancer antigen-specific CD8$^+$ T cells by using a peptide of the selected epitope, and to a method for mass proliferating CD8$^+$ T cells by using the method.

Since CD8$^+$ T cells have relatively simple functions than other cells such as dendritic cells, CD4$^+$ T cells, and NK cells, it is less likely to cause unexpected side effects during anticancer immunotherapy. Generally, antigen-specific CD8$^+$ T cells are isolated by using MHC class I/peptide multimer, but the method has a drawback in that due to the high cell death rate caused by cell apoptosis after cell isolation, a long period of culture is required to produce a sufficient amount of antigen-specific CD8$^+$ T cells. Accordingly, needed is a surrogate marker which can isolate antigen-specific CD8$^+$ T cells instead of MHC multimer which stimulates a T cell receptor (TCR). Thus, the present inventors have been studying for a long time about the immune regulatory protein, i.e. 4-1BB (CD137).

It has been known that 4-1 BB, which is expressed in T cells activated by an inducible costimulatory molecule, particularly enhances a CD8$^+$ T cell activity and as well as increases expression of anti-apoptotic molecules such as Bcl-2, Bcl-XL, and Bfl-1 so that activation-induced cell death (AICD) is inhibited. The characteristic of 4-1BB simulation are suitable for cancer treatment. Thus, based on the characteristic, a therapeutic effect of an anti-4-1BB mAb on a cancer is validated by using an animal model. In the previous study, the present inventors have established a method for isolating and proliferating antigen-specific CD8 1 T cells by using the anti-4-1BB antibody on the basis of 4-1BB expression of activated CD8$^+$ T cells in an antigen-specific manner (see Korean registered patent No. 10-0882445). However, in vitro and in vivo half life of an antibody are long, and the total result is shown as combination of a signal transduction result through an Fe receptor and a signal transduction effect through a target protein recognized by the antibody. In addition, in many cases, there are various antibodies for the same antigen, and the antibodies show effects having little differences from each other. To overcome this limitation, it has been developed a method for successfully isolating and proliferating antigen-specific CD8$^+$ T cells by using the pentamer, COMP-4-1BBL protein (see Korean registered patent No. 10-1103603).

Those two patents relate to techniques for isolating/mass-culturing CD8 T cells specific for a viral antigen (e.g., EBV/LMP2A, CMV/pp65) which is a heterologous antigen, and the techniques are relatively easy to implement because the in vivo ratio of those cells are high. However, since most of cancer cells are formed by cells which compose our bodies, it is necessary to selectively isolate and mass culture CD8 T cells which recognize an autologous cancer antigen (self-tumor Ag), wherein the autologous cancer antigen is a protein to form the body and overexpressed in cancer cells while present in a low ratio in normal cells.

SUMMARY OF THE INVENTION

Thus, an object of the present invention is to provide a method for isolating and proliferating autologous cancer antigen-specific CD8$^+$ T cells which makes it possible to selectively isolate and mass culture autologous cancer antigen-specific CD8$^+$ T cells within 31 days, wherein, the autologous cancer antigen is present in the body in an extremely low ratio.

To achieve the object, the present invention provides a method for isolating autologous cancer antigen-specific CD8$^+$ T cells, the method including: a) selecting a CD8$^+$ T cell epitope of the autologous cancer antigen present in blood of a cancer patient; b) culturing a peripheral blood mononuclear cell (PBMC) isolated from blood of the cancer patient in a medium together with a peptide of the epitope and IL-2; c) inducing 4-1BB expression in the cultured cells by adding the peptide same as in step b); and d) culturing cells in which 4-1BB expression is induced on a culture plate coated with an anti-4-1BB antibody, and removing unattached cells.

In the isolation method of the present invention, the autologous cancer antigen in step a) may be selected from the group consisting of hTERT, WT1, NY-ESO1 and MAGE-A3.

In the isolation method of the present invention, the epitope in step b) may be a peptide formed by an amino acid sequence selected from the group consisting of SEQ ID NOs: 1 to 15.

In the isolation method of the present invention, the induction of expression in step c) may be performed for 12 to 36 hours with culturing.

In the isolation method of the present invention, the culture in step d) may be performed for 1 to 20 minutes.

Further, the present invention provides a method for mass culturing autologous cancer antigen-specific CD8$^+$ T cells, the method including: suspending autologous cancer antigen-specific CD8$^+$ T cells isolated by the method and allogenic PMBCs irradiated with radiation in a medium including IL-2, an anti-CD3 antibody, and autoplasma; and then injecting the suspension into a culture bag; and additionally injecting the medium and culturing.

In the mass culture method of the present invention, the PBMC may be isolated from a healthy donor.

In the mass culture method of the present invention, the culture may be performed for 4 to 15 days.

According to the present invention, it is possible to isolate autologous cancer antigen-specific $CD8^+$ T cells by using the peptide of the CD8 T cell epitope of the autologous cancer antigen present in blood of individual cancer patients instead of the heterologous antigen. Therefore, by using the T cell, which is isolated by the method of the present invention and recognizes the autologous cancer antigen present in an extremely low ratio in a healthy person, it is possible to effectively select and eliminate cancer cells derived from the cancer patient's own cells.

BRIEF DESCRIPTION OF THE DRAWINGS

FIG. 3 shows an hTERT epitope screening result using PBMCs obtained from a healthy donor.

DETAILED DESCRIPTION OF PREFERRED EMBODIMENTS

Figure 1:
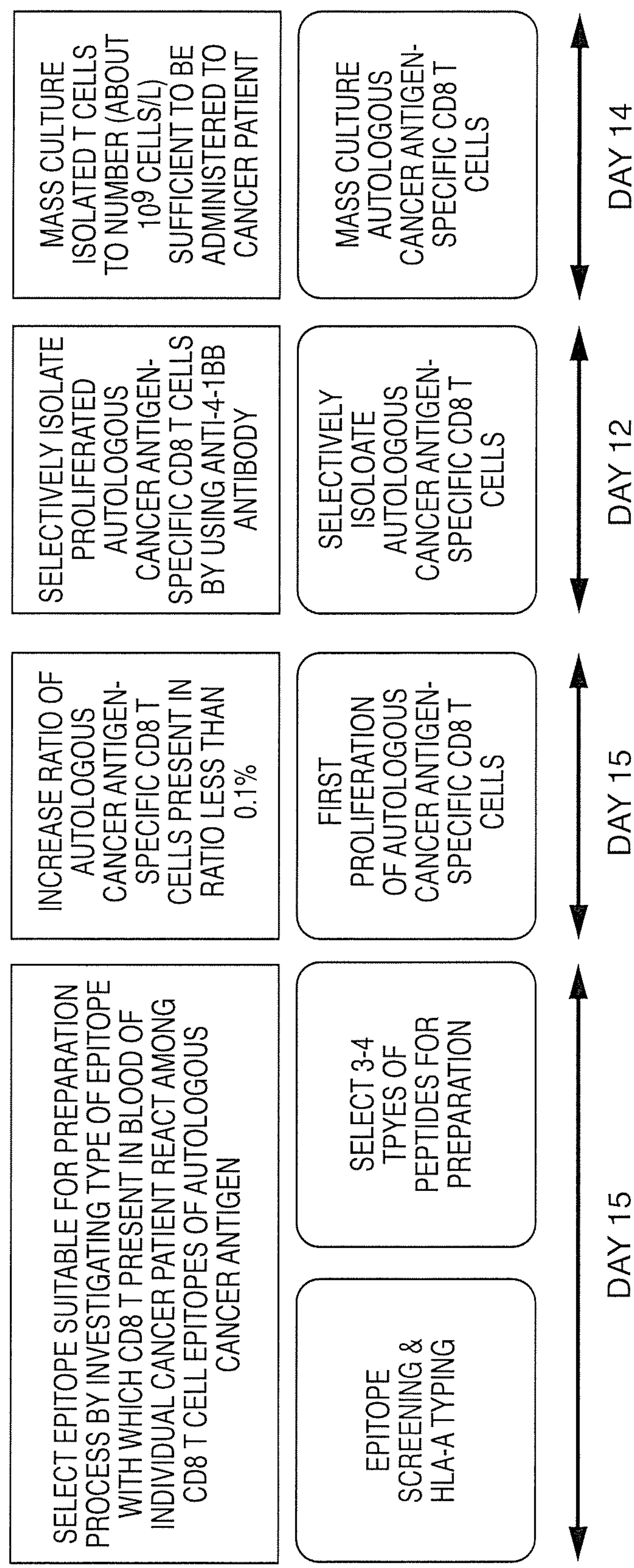
FIG. 1 illustrates a process of selectively isolating and mass culturing autologous cancer cell-specific CD8+ T cells according to the present invention.

Since cancer cells are derived from cells which form our body, it is necessary to selectively isolate and mass culture $CD8^+$ T cells specific for an autologous cancer antigen (self-tumor Ag), which is overexpressed in cancer cells, to selectively eliminate cancer cells. However, a T cell, which recognizes the autologous cancer antigen, is present in an extremely low ratio in a healthy person with an activity which is inhibited by immune tolerance. Accordingly, it has not been yet developed a standardized process of selectively isolating and mass culturing autologous cancer antigen-specific $CD8^+$ T cells from blood of a cancer patient. Thus, the present inventors have been developed a standardized technique of a process of selectively isolating and mass culturing $CD8^+$ T cell within 31 days by using an anti-4-1BB antibody, wherein the $CD8^+$ T cell is present in the body in an extremely low ratio and specific for an autologous cancer antigen such as hTERT, WT1, NY-ESO1, and MAGE-A3.

Therefore, the present invention provides a method for isolating autologous cancer antigen-specific $CD8^+$ T cells. Specifically, the method for isolating autologous cancer antigen-specific $CD8^+$ T cells of the present invention includes: a) selecting a $CD8^+$ T cell epitope of the autologous cancer antigen present in blood of a cancer patient; b) culturing a peripheral blood mononuclear cell (PBMC) isolated from blood of the cancer patient in a medium together with a peptide of the epitope and IL-2; c) inducing 4-1BB expression in the cultured cells by adding the peptide same as in step (b); and d) culturing cells, in which 4-1BB expression is induced, on a culture plate coated with an anti-4-1BB antibody, and removing unattached cells.

In the isolation method of the present invention, the autologous cancer antigen in step a) may be any cancer antigen present in the cancer patient's own body, and a suitable autologous cancer antigen may be selected and used depending on the type of cancer. Preferably, hTERT (GenBank: BAC11010.1), WT1 (GenBank: AAO61088.1), NY-ESO1 (GenBank: CAA05908.1), and MAGE-A3 (NCBI Reference Sequence: NP 005353.1), etc. may be used as a typical autologous cancer antigen used in anticancer immunotherapy. The hTERT is an enzyme for synthesizing telomeric DNA at the end of a chromosome and known as a target antigen for various solid cancers including lung cancer, gastric cancer and pancreatic cancer because cancer cells over-activate the enzyme to avoid telomerase-dependent cell death (see Kim N W, et al. Science. 1994; 266: 2011-2015). Also, the WT1, which is a gene associated with Wilms tumor, encodes a zinc-finger transcriptional factor which is a protein involved in cell proliferation and differentiation, apoptosis, and development of an organ and kwon as a target antigen of brain and spinal cancer, and lung cancer, etc. (see Call K M, et al., *Cell.* 1990. 60:509-520; Nakahara Y, et al., *Brain Tumor Pathol.* 2004. 21:113-6). In addition, the NY-ESO1, one of the proteins belonging to a cancer testis antigen (CTA), has been known to be expressed in various cancer cells including germ cell cancer, sarcoma, and breast cancer; however, it has not been well known about functions of NY-ESO1 in those cells (see Gnjatic S, et al., *Adv Cancer Res.* 2006; 95:1-30). The MAGE-A3 is a protein belonging to melanoma-associated antigen family. Although any function of the MAGE-A3 in normal cells has not found, it has been known that MAGE-A3 is overexpressed in various cancer cells including lung cancer, sarcoma, and melanoma so that MAGE-A3 is assessed as a target antigen suitable for immunotherapy of a cancer (see Decoster L, et al., *Ann Oncol.* 2012 June; 23(6):1387-93).

In the isolation method of the present invention, the epitope in step b) may be a peptide formed by an amino acid sequence selected from the group consisting of SEQ ID NOs: 1 to 15.

In the isolation method of the present invention, the medium in step b) may be a medium including autoplasma, and the culture in step b) may be performed for 12 to 16 days.

In the isolation method of the present invention, the induction of expression in step c) may be performed for 12 to 36 hours with culturing, and the culture in step d) may be performed for 1 to 20 minutes.

Further, the present invention provides a method for mass culturing autologous cancer antigen-specific $CD8^+$ T cells, the method including: suspending autologous cancer antigen-specific $CD8^+$ T cells isolated by the isolation method described above, and allogenic PMBCs irradiated with radiation in a medium including TL-2, an anti-CD3 antibody, and autoplasma, and then injecting the suspension into a culture bag; and additionally injecting the medium and culturing.

In the mass culturing method of the present invention, the PBMCs may be isolated from a normal donor, and the culture may be performed for 4 to 15 days. In particular, during the culture, the medium may be additionally injected on day 4, 7, 9, 11 and 14 of culture.

Hereinafter, the method for isolating and proliferating autologous cancer antigen-specific CD8$^+$ T cells of the present invention will be described in stepwise.

(1) Epitope Screening (Pre-Selection Test)

According to the present invention, autologous cancer antigen-specific CD8 T cells are selectively isolated and proliferated by using a peptide. Since epitopes of an autologous cancer antigen recognized by a CD8 T cell are different depending on HLA-A types and status of individual patients, a CD8 T cell epitope of the autologous cancer antigen present in blood of individual patients is selected through epitope screening so that 3-4 types of peptides for preparing a T cell therapeutic agent are selected.

(2) Proliferation of Autologous Cancer Antigen-Specific CD8 T Cells

Since autologous cancer antigen-specific CD8 T cells are present in blood in 0.1% or less, 3-4 types of peptides for preparation and IL-2 are added to PBMCs isolated from blood, and the mixture is culture for 14 days to induce proliferation of CD8 T cells specific for a peptide derived from the autologous cancer antigen. On day 14 of culture, whole cells are collected and reactivated with the same peptides for 24 hours to induce peptide-specific CD8 T cells to simultaneously express 4-1BB.

(3) Selective Isolation of Autologous Cancer Antigen-Specific CD8 T Cells

Cells reactivated with the peptide are seeded to a culture plate coated with an anti-4-IBB antibody and cultured for 10 minutes to allow CD8 T cells expressing 4-1BB to be attached. Then, unattached cells are entirely removed through washing. Thereafter, IL-2-containing medium is added and culture is then performed for two days to proliferate the isolated T cells and also to allow the T cells to be detached from the culture plate.

(4) Mass Culture of Autologous Cancer Antigen-Specific CD8 T Cells

In a 1 L culture bag, $5\times10^5$ of isolated CD8 T cells, $1\times10^8$ of irradiated allogenic PBMC cells, 1000 U/ml of IL-2, and 40 ng of an anti-CD3 mAb are mixed, and the medium is periodically added for 14 days to culture cells to a degree of about $10^9$ cells/L such that the cells are proliferated to a level sufficient to be administered to a cancer patient.

Hereinafter, the present invention will be described in more detail with reference to the following examples. However, these examples are only provided to more specifically describe the present invention, and the scope of the invention is not limited thereto.

Experimental Example. Epitope Screening Process

Figure 2:
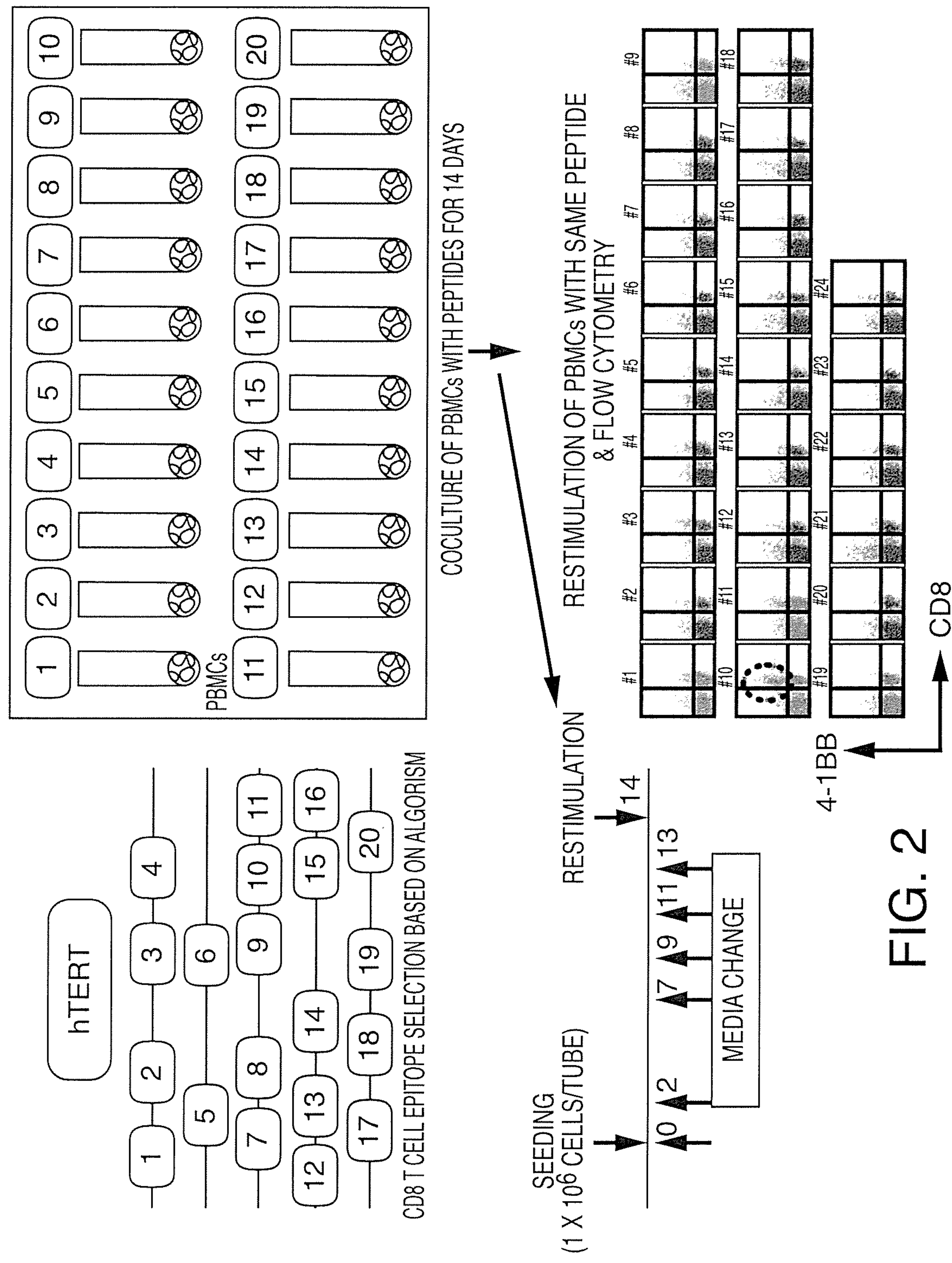
FIG. 2 is a flow chart showing a process of epitope screening according to the present invention.

CD 8 T cell epitopes of an autologous cancer antigen were selected through algorithm. To evaluate a type of CD8 T cell epitope with which T cells present in blood of a cancer patient react, peripheral blood mononuclear cells (PBMCs) were isolated from blood of the cancer patient, washed, and suspended in CTL medium (RPMI1640 medium+4 mM L-glutamine+12.5 mM HEPES+50 μM 2-mercaptoethanol+3% autoplasma) to become the concentration of $1\times10^6$ cell/ml. Then, 1 ml of the suspension was aliquoted in a 14 ml round tube. Peptides for each epitope selected by the analysis with algorithm were added to each tube in the concentration of 1 μg/ml. Thereafter, culture in a $CO_2$ incubator was started. Two days after culture, 1 ml of CTL medium including 50 U/ml IL-2 was added to each tube. On day 7, 9, 11, and 13 of culture, 1 ml of the medium was removed and CTL medium including 50 U/ml IL-2 was added. On day 14 of culture, RPMI1640 medium was added to each tube, and the tube was centrifuged for 5 minutes at 1400 rpm. Then, cells were washed three times. Washed cells were suspended in 1 ml CTL medium, and the same peptide was added in the concentration of 5 μg/ml. Thereafter, the resultant was cultured. After 24 hours, cells in each tube were collected and stained with an anti-CD8-PE-Cy5 and anti-4-1BB-PE antibodies for flow cytometry. Then, by analyzing a ratio of CD8 T cell expressing 4-1BB, a type of peptide which CD8 T cell reacted with and was thus activated has been determined. FIG. 2 is a flow chart showing an epitope screening process according to the present invention.

The anti-CD8-PE-Cy5 and anti-4-1BB-PE used in the experiment were purchased from eBioscience (San Diego, Calif., USA). RPMI1640, L-glutamine, HEPES, and 2-mercaptoethanol were purchased from Invitrogen (San Diego, Calif., USA).

Example 1 Selection of Autologous Cancer Antigen and CD8 T Cell Epitope

Based on journals (Scanlan M J, et a., *Immunol Rev.* 2002 Oct. 188:22-32; Ramakrishnan S, et al., *Cancer research.* 1998. 58:622-625; Nakahara Y, et al., *Brain Tumor Pathol.* 2004. 21(3):113-6) evaluating which type of cancer antigen is suitable for immunotherapy of a cancer depending on the type of cancer, an autologous cancer antigen, which is suitable for immunotherapy of frequently occurring cancer in Korean and hard-to treat cancers (e.g., gastric cancer, lung cancer and pancreatic cancer), is selected. hTERT (GenBank: BAC11010.1), WT1 (GenBank: AA061088.1), NY-ESO1 (GenBank: CAA05908.1), and MAGE-A3 (NCBI Reference Sequence: NP_005353.1) are typical autologous cancer antigens used in anticancer immunotherapy in various ways, and types of cancers to which those four cancer antigens are applicable are selected and summarized in Table 1 below.

TABLE 1

| Target antigen | Patients |
|---|---|
| EBV | |
| EBNA1, LMP1, LMP2 | EBV-related Tumors<br>Gastric Cancer<br>Nasopharyngeal Careinoma<br>Hodgkin's lymphoma<br>Non Hodgkin's lymphoma |
| hTERT | Lung cancer, Gastric cancer,<br>Pancreatic cancer, melanoma,<br>and other solid cancers |
| WT-1 | Ghoblastoma, lung cancers<br>Leukemia |
| NY-ESO-1 | Ovarian cancer, Sarcoma |
| MAGE-3 | Sarcoma, Lung cancer, Malanoma |

An amino acid sequence of the selected autologous cancer antigen was analyzed through algorithm to determine an amino acid sequence which is expected as a CD8 T cell epitope (CTLPred: http://wv..rw.imtech.res.in/raghava/ctlpred/, NetCTL: http://www.cbs.dtu.dk/services/NetCTL/, SYFPEITHT: http://www.syfpeithi.de/), and a peptide of the selected epitope was chemically synthesized (Peptron Inc; www.peptron.com) and used in epitope screening. CD8 T cell epitopes selected from each autologous cancer antigen are shown in Tables 2 to 5 below.

TABLE 2

(SEQ ID NOS 16, 1, 17-22, 2-3, and 23-50, respectively, in order of columns)
Amino acid sequence of hTERT CTL epitopes

| | |
|---|---|
| hTERT-1 AAFRALVAQCL | hTERT-21 QTQLSRKLP |
| hTERT-2 CLKELVARV | hTERT-22 ALEAAANPAL |
| hTERT-3 LAFGFALL | hTERT-23 ILAKFLHWL |
| hTERT-4 VGDDVLVH | hTERT-24 RLVDDFLLV |
| hTERT-5 FVLVAPSCA | hTERT-25 EARPALLTSRL RFIPK |
| hTERT-6 GAATQARP | hTERT-26 RLFFYRKSV |
| hTERT-7 SGTRHSH | hTERT-27 YLFFYRKSV |
| hTERT-8 KEQLRPSFLLSSLRPSL | hTERT-28 DLQVNSLQTV |
| hTERT-9 PLFLELL | hTERT-29 YLQVNSLQTV |
| hTERT-10 AAVTPAA | hTERT-30 GLLGASVLGL |

TABLE 2-continued (SEQ ID NOS 16, 1, 17-22, 2-3, and 23-50, respectively, in order of columns)
Amino acid sequence of hTERT CTL epitopes

| | |
|---|---|
| hTERT-11 QSIGIRQ | hTERT-31 ALLTSRLRFI |
| hTERT-12 IVNMDYV | hTERT-32 RLTSRVKAL |
| hTERT-13 RPGLLGASV | hTERT-33 TYVPLLGSL |
| hTERT-14 TLTDLQP | hTERT-34 CYGDMENKL |
| hTERT-15 LLCSLCYG | hTERT-35 AYQVCGPP |
| hTERT-16 LVRGVPEYGCVVNLR | hTERT-36 VYGFVRACL |
| hTERT-17 YSSYARTSIRASL | hTERT-37 VYAETKHFL |
| hTERT-18 IYKILLLQAY | hTERT-38 DYVVGARTF |
| hTERT-19 LGAKGAA | |
| hTERT-20 YVPLLGSL | |

TABLE 3

(SEQ ID NOS 51-55, 6, 56, 7, 57-66, respectively, in order of columns)
Amino acid sequence of WT1 CTL epitopes

| HLA-A type | Amino acid sequence | HLA-A type | Amino acid sequence |
|---|---|---|---|
| HLA-A*02 | WT1-1 ALLPAVPSL | HLA-A*24 | WT1-10 QYRIHTHGVF |
| HLA-A*02 | WT1-2 DLNALLPAV | HLA-A*24 | WT1-11 AFTVHFSGQF |
| HLA-A*02 | WT1-3 SLGEQQYSV | HLA-A*24 | WT1-12 RWPSCQKKF |
| HLA-A*02 | WT1-4 RMFPNAPYL | HLA-A*24 | WT1-13 RVPGVAPTL |
| HLA-A*02 | WT1-5 GVFRGIQDV | HLA-A*24 | WT1-14 DFKDCERRF |
| HLA-A*02 | WT1-6 CMTWNQMNL | HLA-A*24 | WT1-15 RTPYSSDNL |
| HLA-A*02 | WTI-7 SGQFTGTAGA | HLA-A*24 | WT1-16 TSEKPFSCR |
| HLA-A*02 | WT1-8 VLDFAPPGA | HLA-A*24 | WT1-17 FSRSDQLKR |
| HLA-A*24 | WT1-9 APGCNKRYF | HLA-A*24 | WT1-18 LSHLQMHSR |

TABLE 4

(SEQ ID NOS 67, 8, 68, 9, 69-71, 10-11, and 72-82, respectively, in order of columns)
Amino acid sequence of NY-ESO-1 CTL epitopes

| HLA-A type | Amino acid sequence | HLA-A type | Amino acid sequence |
|---|---|---|---|
| HLA-A*02 | NY-1 SLAQDAPPL | HLA-A*24 | NY-11 EFTVSGNIL |
| HLA-A*02 | NY-2 SISSCLQQL | HLA-A*24 | NY-12 SGLNGCCR |
| HLA-A*02 | NY-3 LLMWITQCFL | HLA-A*24 | NY-13 SSCLQQLSL |
| HLA-A*02 | NY-4 RLLEFYLAM | HLA-A*24 | NY-14 FATPMEAEL |
| HLA-A*02 | NY-5 DAPPLPVPGV | HLA-A*24 | NY-15 ITQCFLPVF |
| HLA-A*02 | NY-6 TVSGNILTI | HLA-A*24 | NY-16 LTAADHRQL |
| HLA-A*02 | NY-7 QLQLSISSCL | HLA-A*24 | NY-17 YLAMPFATPM |

TABLE 4-continued (SEQ ID NOS 67, 8, 68, 9, 69-71, 10-11, and 72-82, respectively, in order of columns)
Amino acid sequence of NY-ESO-1 CTL epitopes

| HLA-A type | Amino acid sequence | HLA-A type | Amino acid sequence |
|---|---|---|---|
| HLA-A*02 | NY-8 GVLLKEFTV | HLA-A*24 | NY-18 ATPMEAELAR |
| HLA-A*02 | NY-9 ILTIRLTAA | HLA-A*24 | NY-19 ASGPGGGAPR |
| HLA-A*02 | NY-10 SLLMWITQC | HLA-A*24 | NY-20 PVPGVLLKEF |

TABLE 5

(SEQ ID NOS 83, 12, 84, 13, 85-88, 14-15, and 89-102 respectively, in order of columns)
Amino acid sequence of MAGE-A3 CTL epitopes

| HLA-A type | Amino acid sequence | HLA-A type | Amino acid sequence |
|---|---|---|---|
| HLA-A*02 | M3-1 ALSRKVAEL | HLA-A*24 | M3-13 VFEGREDSIL |
| HLA-A*02 | M3-2 LLIIVLAII | HLA-A*24 | M3-14 EGLEARGEAL |
| HLA-A*02 | M3-3 GLLIIVLAI | HLA-A*24 | M3-15 TFPDLESEF |
| HLA-A*02 | M3-4 KIWEELSVL | HLA-A*24 | M3-16 EFLWGPRAL |
| HLA-A*02 | M3-5 ILGDPKKLL | HLA-A*24 | M3-17 VAELVHFLL |
| HLA-A*02 | M3-6 TLVEVTLGEV | HLA-A*24 | M3-18 IFSKASSSL |
| HLA-A*02 | M3-7 ALVETSYVKV | HLA-A*24 | M3-19 KVLHHMVKI |
| HLA-A*02 | M3-8 AALSRKVAEL | HLA-A*24 | M3-20 VDPIGHLYI |
| HLA-A*02 | M3-9 LVFGIELMEV | HLA-A*24 | M3-21 IMPKAGLLI |
| HLA-A*02 | M3-10 SLPTTMNYPL | HLA-A*24 | M3-22 SILGDPKKL |
| HLA-A*24 | M3-11 SYPPLHEWVL | HLA-A*24 | M3-23 VKISGGPHI |
| HLA-A*24 | M3-12 YIFATCLGL | HLA-A*24 | M3-24 LGLSYDGLL |

Example 2. Epitope Screening on Clinical Cancer Patient

To evaluate whether CD8 T cell epitopes of autologous cancer antigens, i.e. hTERT, WT1, NY-ESO1, and MAGE-A3, selected in Example 1 substantially induce proliferation of CD8 T cells present in blood of a clinical cancer patient, epitope screening as depicted in FIG. 2. was performed. hTERT epitope screening was performed on gastric cancer, lung cancer and pancreatic cancer, as a main subject matter. Also, WT1 epitope screening was performed on brain and spinal cancer and lung cancer; NY-ESO1 epitope screening was performed on ovarian cancer and sarcoma; and MAGE-A3 epitope screening was performed on sarcoma and lung cancer as a main subject matter.

FIG. 3 shows an hTERT epitope screening result using PBMCs obtained from a healthy donor.

Figure 4:
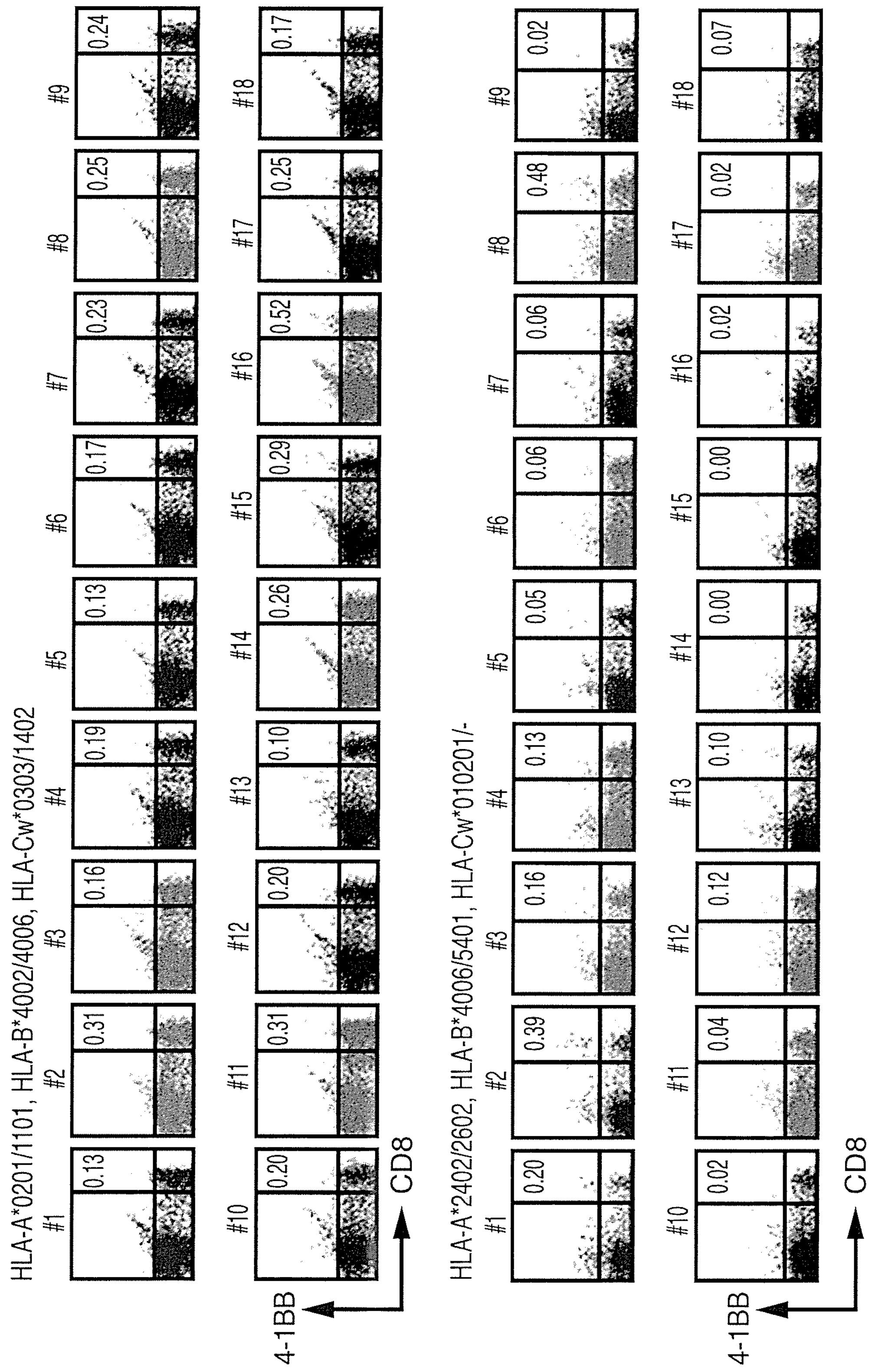
FIG. 4 shows a WT1 epitope screening result using PBMCs obtained from the healthy donor.

FIG. 4 shows a WTI epitope screening result using PBMCs obtained from the healthy donor.

As shown in FIGS. 3 and 4, CD8 T cell epitopes of hTERT and WT1 did not induce T cell response by PBMCs derived from blood of the healthy donor. Thus, it has been found that the selected epitope of the present invention cannot be recognized by T cells of the healthy donor.

Figure 5:
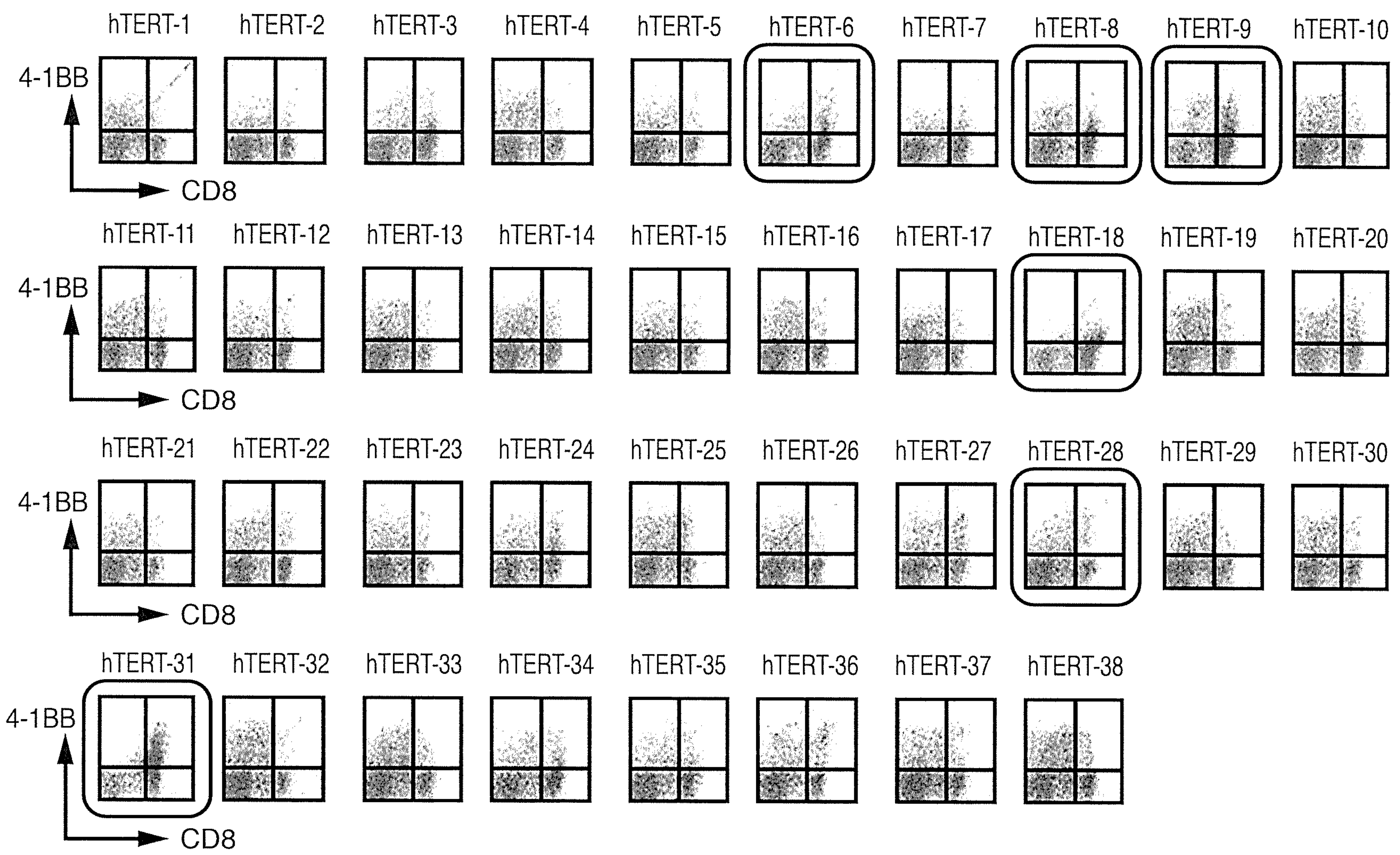
FIGS. 5 to 7 show hTERT epitope screening results using PBMCs respectively obtained from patients with gastric cancer, lung cancer and pancreatic cancer.
Figure 6:
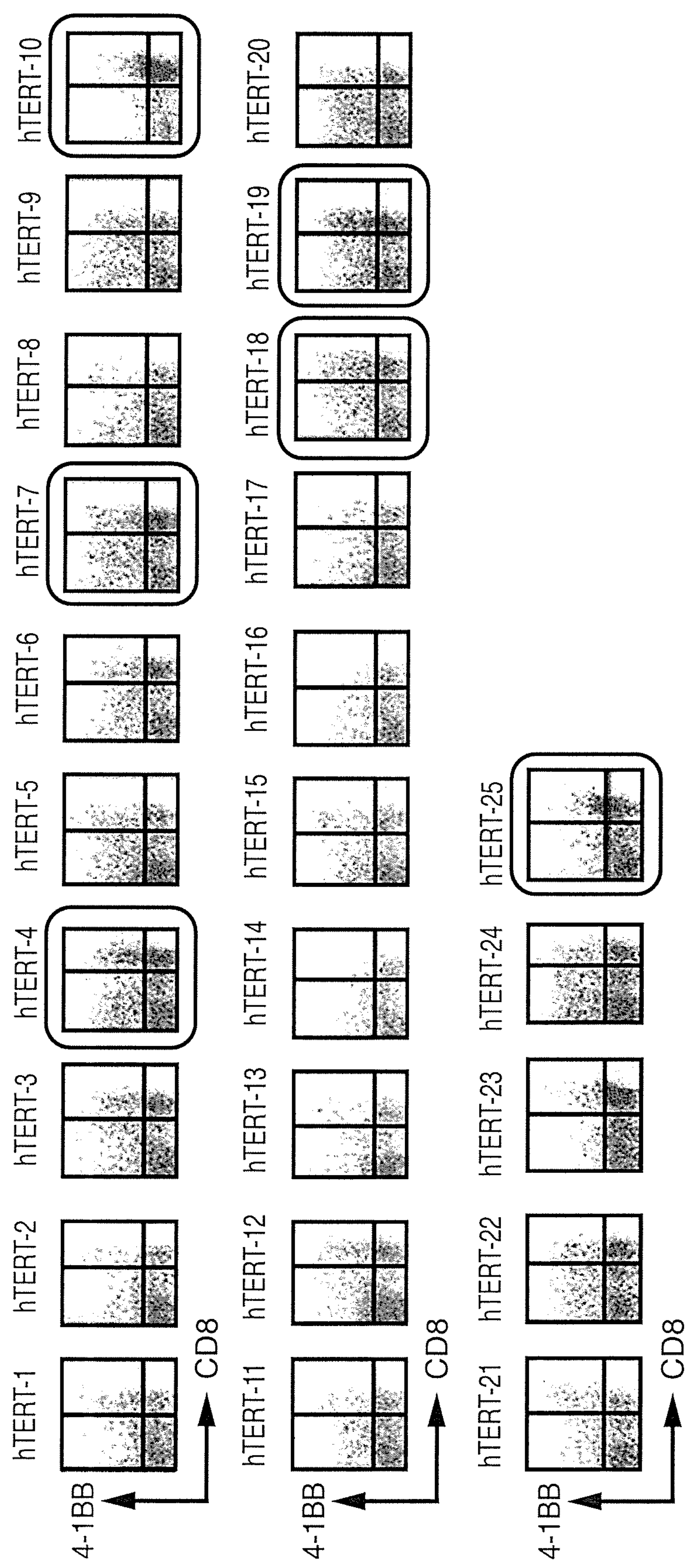
Figure 7:
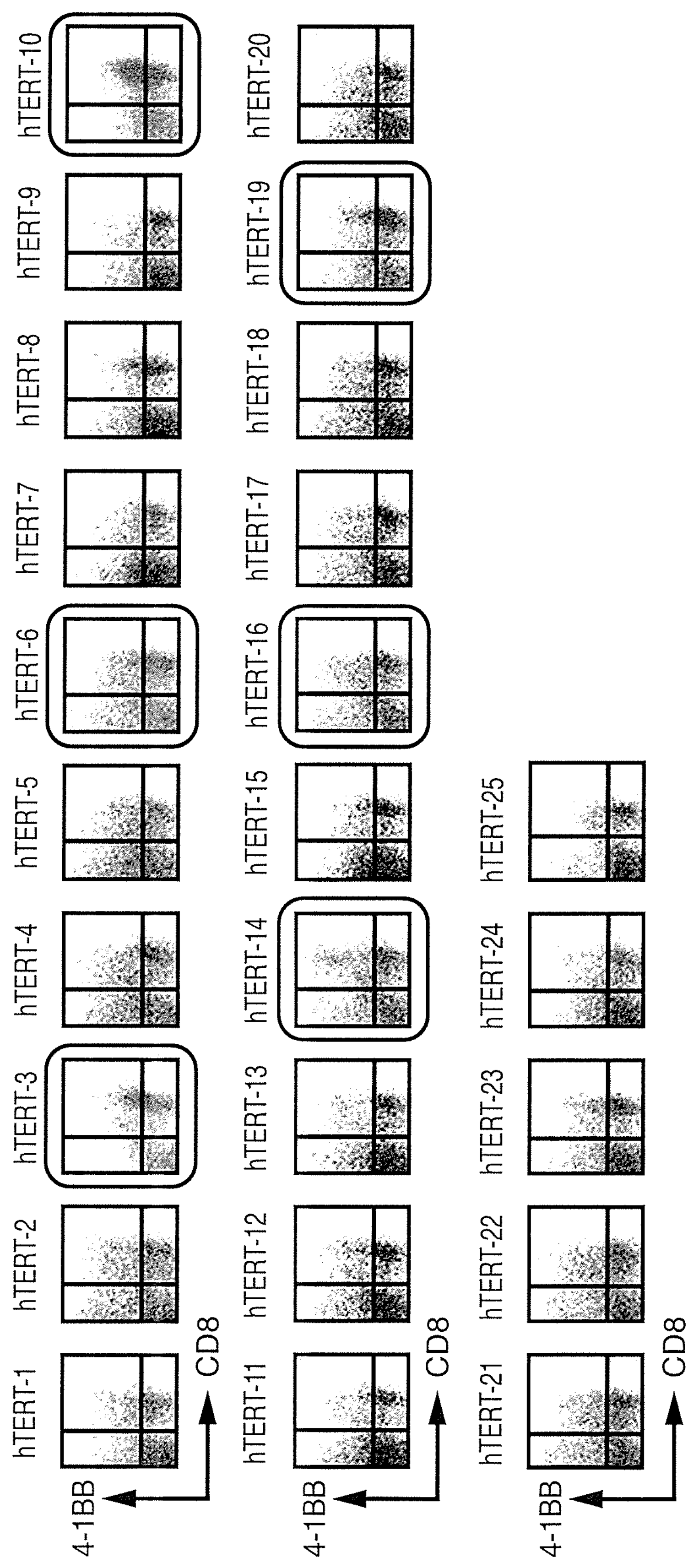

FIGS. 5 to 7 show hTERT epitope screening results using PBMCs respectively obtained from patients with gastric cancer, lung cancer and pancreatic cancer.

Figure 8:
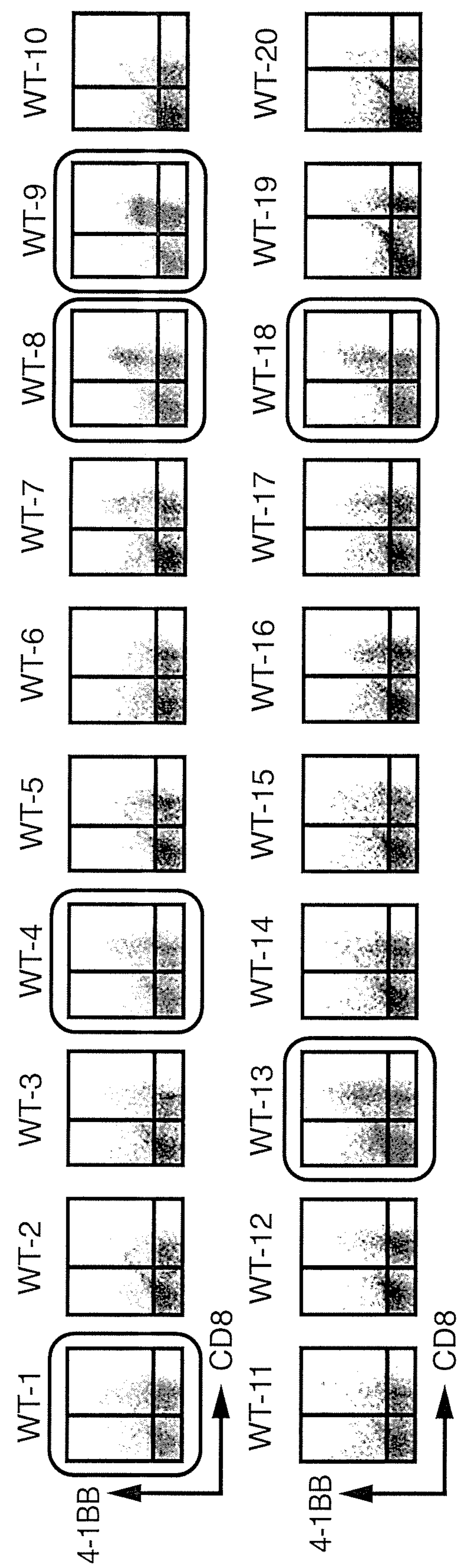
FIGS. 8 and 9 show WT1 epitope screening results using PBMCs respectively obtained from patients with glioblastoma and lung cancers.
Figure 9:
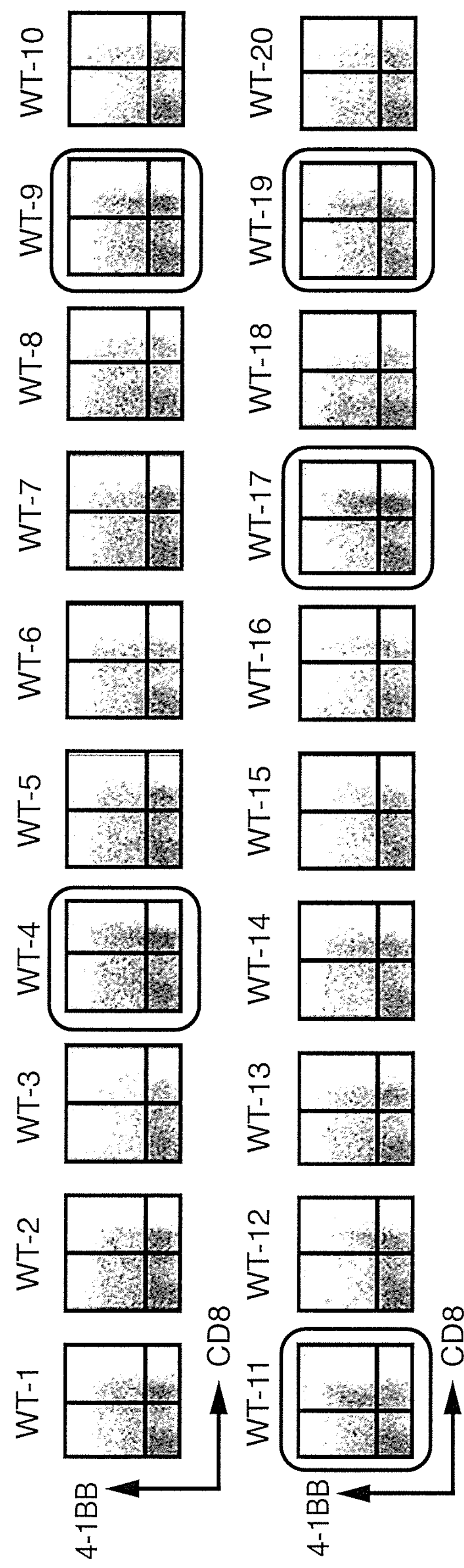

FIGS. 8 and 9 show WT1 epitope screening results using PBMCs respectively obtained from patients with glioblastoma and lung cancers.

Figure 10:
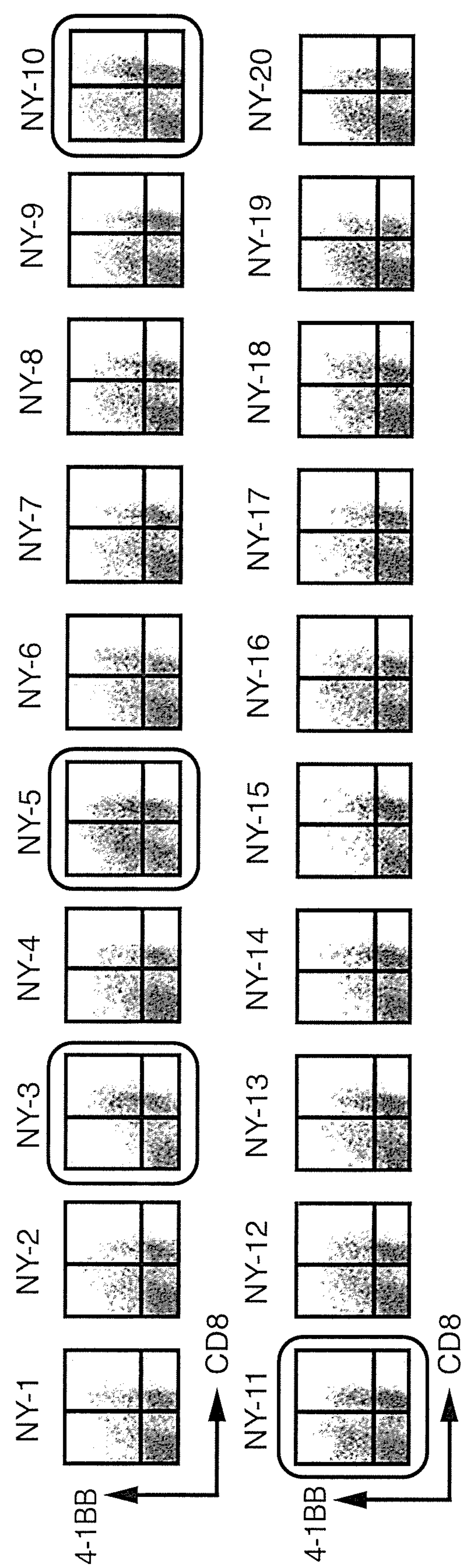
FIGS. 10 and 11 show NY-ESO1 epitope screening results using PBMCs respectively obtained from patients with ovarian cancer and sarcoma.
Figure 11:
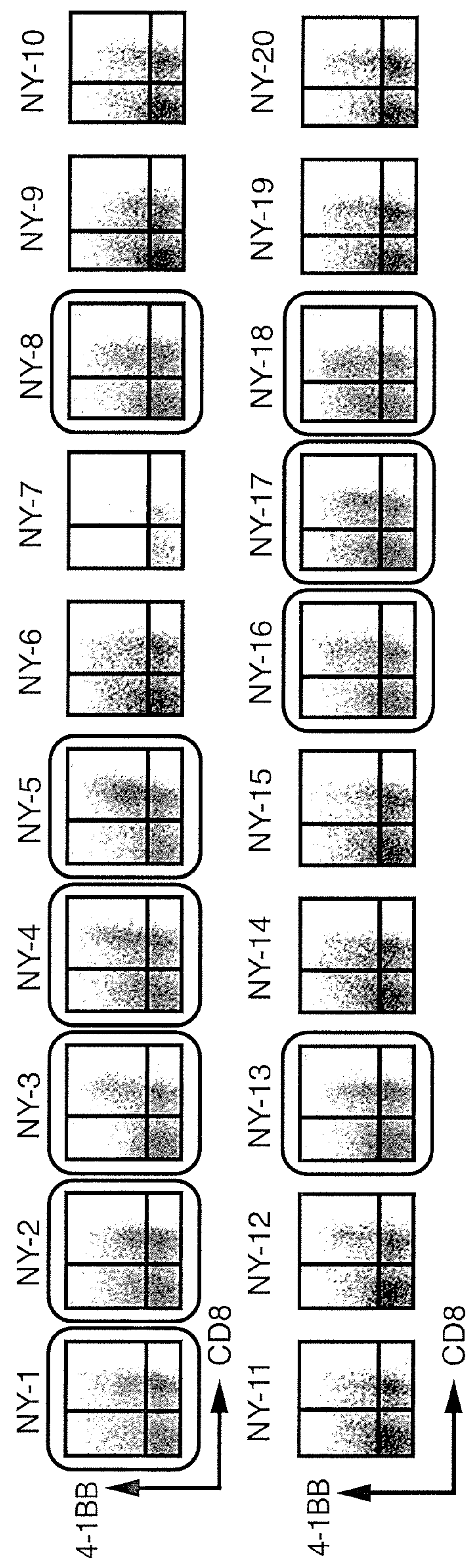

FIGS. 10 and 11 show NY-ESO1 epitope screening results using PBMCs respectively obtained from patients with ovarian cancer and sarcoma.

Figure 12:
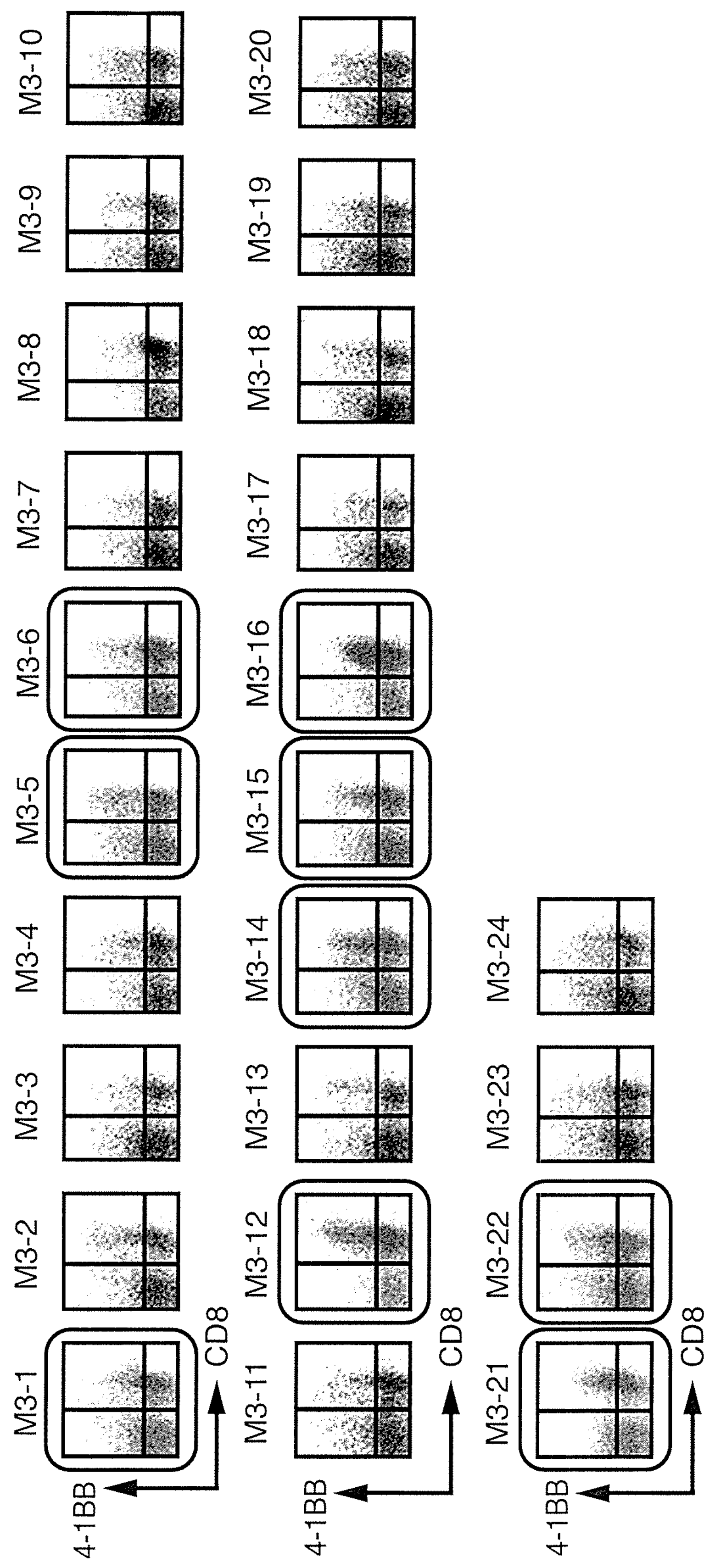
FIGS. 12 and 13 show MAGE-A3 epitope screening results using PBMCs respectively obtained from patients with sarcoma and lung cancers.
Figure 13:
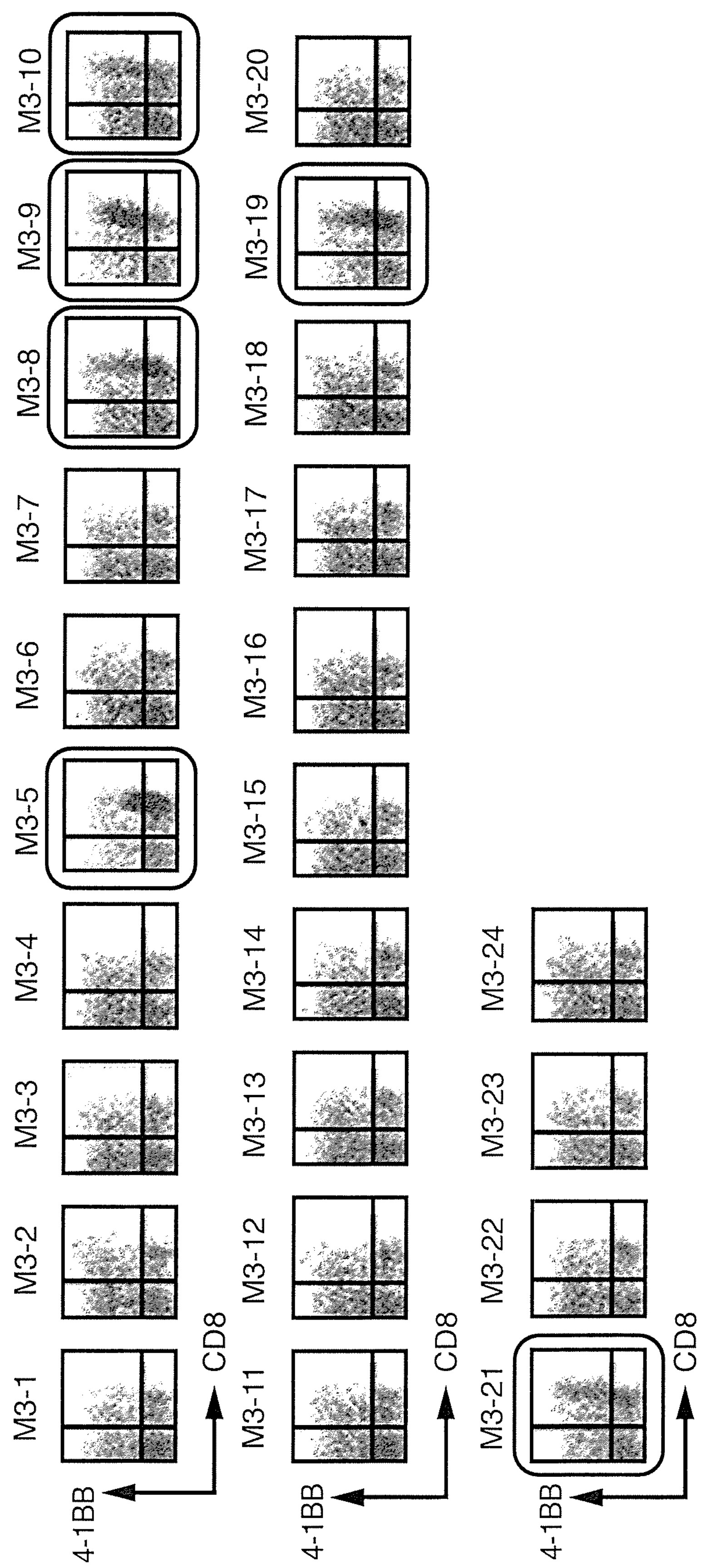

FIGS. 12 and 13 show MAGE-A3 epitope screening results using PBMCs respectively obtained from patients with sarcoma and lung cancers.

As shown in FIGS. 5 to 13, as a result of investigating reactivity of CD8 T cells on hTERT, WT1, NY-ESO1, and MAGEA3 by performing epitope screening on PBMCs isolated from blood of the clinical cancer patient, it has been found that in contrast with the result in the health donor, high degree of T cell response was exhibited to the selected autologous cancer antigens. Reactivity on each autologous cancer antigen was then evaluated by repeatedly performing epitope screening on gastric cancer, lung cancer, sarcoma, and ovarian cancer.

In addition, to objectively analyze the epitope screening result, a scoring system was made as shown in Table 6 below.

TABLE 6

| Score | The ratio of 4-1BB⁻CD8⁺ T cells | The ratio of CD8⁺ T cells (compare with average ratio of CD8⁻ T) |
|---|---|---|
| 0 | 0-3% | <1.0 fold |
| 1 | 0-3% | ≥1.0 fold |
| 2 | 4-10% | ≥1.0 fold |
| 3 | 11-15% | ≥1.0 fold |
| 4 | 16-20% | ≥1.0 fold |
| 5 | >20% | ≥1.0 fold |

Although CD8⁺ T cells express the 4-1BB on their surface, in case that the percentage of CD8⁺ T cells is lower than average ratio one point will be deducted from final scores According to the criteria in Table 6 above, the epitope screening results were analyzed, and the analyzed results were shown in Tables 7 to 15 below.

Table 7 below shows the result of analyzing hTERT epitope screening using PBMCs obtained from a patient with gastric cancer.

TABLE 7

| Patients | # Peptide | | | | | | | | | | | | | | | | | | |
|---|---|---|---|---|---|---|---|---|---|---|---|---|---|---|---|---|---|---|---|
| | 11 | 12 | 13 | 14 | 15 | 16 | 17 | 18 | 19 | 10 | 11 | 12 | 13 | 14 | 15 | 16 | 17 | 18 | 19 |
| 1 KYH | 2 | 1 | 2 | 1 | 2 | 1 | 0 | 2 | 2 | 1 | 3 | 2 | 0 | 2 | 1 | 1 | 1 | 1 | 1 |
| 2 SKP | 1 | 1 | 1 | 2 | 1 | 0 | 1 | 1 | 1 | 1 | 1 | 1 | 1 | 1 | 1 | 1 | 1 | 1 | 3 |
| 3 KOS | 3 | 2 | 2 | 2 | 1 | 2 | 2 | 2 | 2 | 2 | 2 | 2 | 1 | 2 | 2 | 2 | 2 | 3 | 2 |
| 4 JHT | 1 | 0 | 1 | 1 | 1 | 1 | 2 | 1 | 1 | 0 | 1 | 1 | 1 | 1 | 1 | 0 | 1 | 1 | 1 |
| 5 ADS | 4 | 1 | 0 | 1 | 0 | 0 | 0 | 0 | 3 | 0 | 0 | 2 | 0 | 4 | 1 | 3 | 3 | 2 | 2 |
| 6 PBO | 2 | 1 | 2 | 1 | 2 | 1 | 1 | 3 | 1 | 1 | 1 | 2 | 1 | 1 | 1 | 0 | 2 | 2 | 5 |
| 7 LHK | 4 | 2 | 2 | 4 | 2 | 3 | 2 | 2 | 4 | 4 | 2 | 2 | 5 | 1 | 4 | 4 | 3 | 4 | 4 |
| 8 LOK | 4 | 3 | 4 | 3 | 3 | 3 | 2 | 2 | 5 | 3 | 4 | 3 | 4 | 3 | 3 | 3 | 3 | 3 | 3 |
| 9 LMY | 4 | 0 | 1 | 1 | 1 | 3 | 1 | 1 | 2 | 1 | 1 | 1 | 2 | 1 | 3 | 3 | 2 | 0 | 2 |
| 10 KYI | 3 | 1 | 3 | 2 | 1 | 4 | 4 | 1 | 4 | 0 | 1 | 1 | 1 | 2 | 0 | 4 | 0 | 2 | 2 |
| 11 LJY | 2 | 1 | 1 | 1 | 1 | 2 | 1 | 1 | 2 | 1 | 1 | 1 | 1 | 2 | 1 | 1 | 1 | 0 | 2 |
| 12 JOM | 2 | 1 | 1 | 3 | 3 | 1 | 1 | 1 | 1 | 2 | 2 | 2 | 3 | 2 | 3 | 1 | 0 | 3 | 2 |
| 13 OYK | 2 | 3 | 1 | 3 | 0 | 0 | 3 | 2 | 2 | 2 | 4 | 1 | 3 | 1 | 0 | 1 | 1 | 1 | 3 |
| 14 HBY | 2 | 1 | 3 | 3 | 3 | 2 | 3 | 2 | 2 | 3 | 2 | 2 | 3 | 2 | 2 | 1 | 3 | 3 | 2 |
| 15 OHS | 5 | 5 | 5 | 5 | 5 | 5 | 5 | 5 | 5 | 5 | 5 | 1 | 5 | 5 | 3 | 3 | 4 | 5 | 5 |
| 16 KYK | 0 | 0 | 0 | 3 | 1 | 0 | 1 | 1 | 2 | 2 | 0 | 3 | 0 | 3 | 2 | 3 | 0 | 0 | 0 |
| 17 KTO | 2 | 1 | 1 | 3 | 2 | 2 | 2 | 2 | 1 | 3 | 3 | 3 | 3 | 3 | 1 | 1 | 2 | 0 | 3 |
| 18 YSM | 1 | 2 | 2 | 1 | 1 | 1 | 1 | 1 | 1 | 3 | 3 | 1 | 3 | 3 | 3 | 1 | 1 | 1 | 1 |
| 19 KIS | 4 | 5 | 4 | 5 | 5 | 1 | 5 | 4 | 5 | 5 | 5 | 5 | 5 | 5 | 4 | 4 | 4 | 4 | 2 |
| 20 JMK | 2 | 0 | 0 | 0 | 0 | 1 | 5 | 0 | 0 | 0 | 0 | 0 | 0 | 0 | 0 | 0 | 0 | 0 | 3 |
| 21 PBO | 1 | 4 | 1 | 1 | 1 | 3 | 2 | 5 | 2 | 1 | 3 | 2 | 1 | 1 | 1 | 1 | 1 | 3 | 1 |
| 22 MSY | 3 | 1 | 1 | 1 | 3 | 2 | 3 | 3 | 3 | 3 | 2 | 0 | 3 | 1 | 1 | 1 | 3 | 0 | 3 |
| 23 KOH | 5 | 4 | 2 | 2 | 1 | 1 | 2 | 1 | 5 | 1 | 3 | 3 | 1 | 1 | 5 | 3 | 2 | 2 | 1 |
| 24 POS | 2 | 5 | 1 | 3 | 0 | 3 | 0 | 0 | 3 | 3 | 2 | 0 | 0 | 4 | 3 | 1 | 0 | 1 | 1 |
| 25 KJO | 2 | 0 | 2 | 0 | 1 | 0 | 2 | 0 | 1 | 2 | 0 | 0 | 2 | 1 | 2 | 0 | 0 | 1 | 0 |
| 26 BUS | 0 | 4 | 2 | 0 | 3 | 0 | 0 | 0 | 0 | 2 | 0 | 0 | 2 | 5 | 1 | 0 | 0 | 0 | 2 |
| 27 OYL | 0 | 0 | 0 | 0 | 0 | 0 | 0 | 0 | 0 | 3 | 0 | 0 | 0 | 0 | 0 | 0 | 3 | 0 | 0 |
| 28 YBS | 3 | 1 | 0 | 0 | 0 | 4 | 0 | 0 | 0 | 3 | 2 | 2 | 0 | 0 | 5 | 3 | 0 | 0 | 0 |
| 29 OJI | 1 | 4 | 0 | 0 | 0 | 3 | 3 | 0 | 1 | 0 | 3 | 0 | 2 | 0 | 2 | 0 | 1 | 3 | 1 |
| 30 IJI | 3 | 3 | 4 | 4 | 3 | 1 | 3 | 3 | 4 | 3 | 0 | 4 | 2 | 3 | 1 | 3 | 1 | 4 | 1 |
| 31 YSJ | 1 | 1 | 1 | 1 | 0 | 1 | 1 | 2 | 1 | 2 | 0 | 1 | 0 | 1 | 1 | 1 | 1 | 1 | 1 |
| 32 LKS | 0 | 2 | 0 | 0 | 0 | 5 | 0 | 0 | 4 | 0 | 0 | 0 | 0 | 0 | 0 | 1 | 0 | 2 | 1 |
| 33 NKO | 1 | 1 | 2 | 0 | 1 | 2 | 2 | 0 | 2 | 0 | 2 | 2 | 1 | 0 | 1 | 1 | 1 | 0 | 2 |
| 34 UMS | 1 | 0 | 2 | 0 | 1 | 0 | 1 | 2 | 2 | 2 | 0 | 0 | 0 | 0 | 0 | 1 | 0 | 0 | 0 |
| 35 YOK | 3 | 1 | 3 | 1 | 1 | 2 | 1 | 1 | 3 | 1 | 1 | 3 | 2 | 1 | 2 | 3 | 3 | 3 | 2 |
| 36 AKJ | 2 | 2 | 2 | 2 | 2 | 2 | 3 | 4 | 2 | 5 | 2 | 2 | 2 | 2 | 3 | 2 | 2 | 2 | 2 |
| 37 PIH | 2 | 1 | 4 | 1 | 1 | 1 | 3 | 2 | 4 | 3 | 2 | 2 | 1 | 3 | 1 | 3 | 1 | 1 | 2 |
| 38 KYS | 2 | 2 | 2 | 4 | 2 | 2 | 2 | 1 | 1 | 2 | 2 | 2 | 3 | 3 | 4 | 1 | 1 | 1 | 2 |
| 39 JJM | 2 | 3 | 3 | 3 | 3 | 3 | 2 | 3 | 3 | 4 | 2 | 3 | 3 | 2 | 5 | 3 | 3 | 2 | 2 |
| 40 NMO | 4 | 3 | 4 | 5 | 3 | 2 | 2 | 3 | 4 | 2 | 2 | 4 | 3 | 5 | 4 | 4 | 3 | 4 | 2 |
| 41 SSS | 2 | 1 | 2 | 1 | 1 | 2 | 3 | 3 | 3 | 3 | 2 | 3 | 2 | 2 | 2 | 1 | 1 | 2 | 3 |
| 42 YKJ | 0 | 2 | 0 | 0 | 2 | 2 | 4 | 0 | 2 | 5 | 2 | 3 | 1 | 1 | 4 | 2 | 2 | 4 | 1 |
| 43 SJK | 1 | 0 | 0 | 3 | 0 | 5 | 0 | 1 | 2 | 1 | 0 | 0 | 0 | 0 | 0 | 1 | 1 | 0 | 0 |
| 44 IYS | 3 | 1 | 2 | 0 | 1 | 1 | 0 | 1 | 0 | 0 | 0 | 0 | 0 | 0 | 1 | 0 | 0 | 1 | 0 |
| 45 JJN | 2 | 2 | 3 | 3 | 3 | 2 | 5 | 2 | 2 | 1 | 3 | 3 | 3 | 3 | 2 | 3 | 3 | 2 | 3 |
| 46 MYJ | 1 | 5 | 5 | 4 | 4 | 4 | 5 | 1 | 4 | 5 | 4 | 5 | 4 | 5 | 5 | 4 | 1 | 3 | 2 |
| 47 NKS | 2 | 0 | 0 | 0 | 0 | 0 | 0 | 0 | 0 | 1 | 3 | 2 | 0 | 3 | 0 | 0 | 0 | 0 | 0 |
| 48 YOK | 0 | 0 | 0 | 0 | 1 | 1 | 2 | 0 | 0 | 2 | 2 | 2 | 0 | 0 | 0 | 1 | 0 | 1 | 0 |
| 49 HKS | 0 | 0 | 2 | 0 | 0 | 3 | 2 | 3 | 4 | 1 | 1 | 0 | 0 | 1 | 0 | 0 | 0 | 3 | 0 |
| 50 PJS | 1 | 0 | 1 | 1 | 0 | 1 | 1 | 1 | 0 | 0 | 0 | 0 | 0 | 0 | 0 | 1 | 1 | 0 | 1 |

TABLE 7-continued

| Patients | # Peptide 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|
| 1 KYH | 2 | 1 | 1 | 2 | 1 | 1 | 0 | 1 | 3 | 2 | 1 | 1 | 1 | 1 | 1 | 2 | 1 | 1 | 2 |
| 2 SKP | 1 | 1 | 1 | 1 | 1 | 1 | 1 | 1 | 2 | 0 | 0 | 0 | 1 | 0 | 1 | 0 | 0 | 0 | 0 |
| 3 KOS | 2 | 2 | 2 | 3 | 2 | 0 | 1 | 2 | 1 | 1 | 2 | 2 | 1 | 0 | 0 | 0 | 0 | 1 | 1 |
| 4 JHT | 1 | 0 | 0 | 1 | 1 | 0 | 1 | 0 | 0 | 0 | 0 | 0 | 1 | 1 | 1 | 0 | 0 | 0 | 1 |
| 5 AHS | 1 | 2 | 2 | 3 | 1 | 2 | 3 | 2 | 0 | 0 | 0 | 1 | 1 | 0 | 0 | 1 | 0 | 0 | 1 |
| 6 POH | 2 | 1 | 2 | 1 | 1 | 2 | 1 | 0 | 1 | 1 | 2 | 1 | 2 | 2 | 1 | 0 | 1 | 0 | 2 |
| 7 LHK | 3 | 2 | 3 | 2 | 2 | 4 | 2 | 3 | 1 | 3 | 2 | 2 | 1 | 0 | 2 | 3 | 1 | 1 | 0 |
| 8 LOK | 4 | 4 | 3 | 3 | 5 | 2 | 3 | 3 | 3 | 4 | 2 | 2 | 4 | 3 | 3 | 2 | 3 | 3 | 4 |
| 9 LMY | 2 | 1 | 1 | 2 | 4 | 1 | 0 | 1 | 3 | 1 | 0 | 0 | 1 | 2 | 2 | 2 | 1 | 1 | 0 |
| 10 KYI | 2 | 0 | 0 | 2 | 2 | 1 | 3 | 4 | 2 | 3 | 3 | 2 | 1 | 1 | 3 | 1 | 0 | 1 | 2 |
| 11 LJY | 1 | 1 | 1 | 1 | 1 | 1 | 1 | 1 | 0 | 0 | 1 | 2 | 2 | 2 | 1 | 1 | 0 | 2 | 1 |
| 12 JOM | 0 | 1 | 1 | 1 | 1 | 1 | 2 | 3 | 3 | 2 | 1 | 1 | 1 | 0 | 0 | 1 | 1 | 0 | 1 |
| 13 CYK | 2 | 0 | 0 | 4 | 1 | 1 | 3 | 3 | 0 | 1 | 2 | 2 | 2 | 1 | 0 | 1 | 1 | 0 | 1 |
| 14 HBY | 3 | 1 | 3 | 2 | 1 | 2 | 1 | 2 | 3 | 3 | 2 | 1 | 2 | 3 | 1 | 2 | 0 | 2 | 2 |
| 15 OMS | 5 | 5 | 4 | 4 | 5 | 3 | 4 | 4 | 4 | 3 | 4 | 4 | 2 | 4 | 2 | 3 | 3 | 3 | 4 |
| 16 KYK | 0 | 2 | 1 | 1 | 0 | 1 | 2 | 2 | 1 | 3 | 3 | 1 | 0 | 2 | 1 | 1 | 1 | 1 | 1 |
| 17 KTO | 3 | 1 | 1 | 2 | 2 | 2 | 2 | 1 | 1 | 2 | 1 | 1 | 0 | 1 | 3 | 1 | 2 | 1 | 1 |
| 18 YSM | 3 | 3 | 3 | 1 | 1 | 1 | 1 | 1 | 1 | 1 | 1 | 1 | 1 | 1 | 0 | 0 | 1 | 1 | 1 |
| 19 KIS | 5 | 5 | 4 | 4 | 5 | 4 | 5 | 5 | 5 | 4 | 1 | 5 | 3 | 4 | 4 | 4 | 5 | 4 | 4 |
| 20 JMK | 0 | 0 | 0 | 0 | 5 | 0 | 0 | 0 | 3 | 0 | 0 | 0 | 0 | 1 | 1 | 0 | 0 | 0 | 0 |
| 21 PBO | 2 | 2 | 2 | 3 | 2 | 1 | 0 | 3 | 2 | 2 | 1 | 3 | 2 | 1 | 0 | 0 | 1 | 2 | 2 |
| 22 HSY | 4 | 2 | 1 | 0 | 1 | 1 | 3 | 4 | 2 | 2 | 1 | 1 | 0 | 1 | 2 | 1 | 0 | 2 | 1 |
| 23 KDH | 1 | 1 | 1 | 4 | 4 | 2 | 2 | 1 | 3 | 2 | 1 | 1 | 1 | 2 | 4 | 1 | 2 | 2 | 1 |
| 24 POS | 1 | 3 | 3 | 0 | 0 | 2 | 1 | 1 | 1 | 1 | 2 | 2 | 4 | 2 | 1 | 1 | 1 | 2 | 2 |
| 25 KJO | 3 | 2 | 1 | 3 | 1 | 2 | 1 | 2 | 2 | 0 | 1 | 2 | 2 | 2 | 1 | 1 | 2 | 2 | 1 |
| 26 BUS | 0 | 3 | 3 | 0 | 0 | 0 | 0 | 0 | 0 | 2 | 1 | 0 | 4 | 2 | 2 | 1 | 2 | 1 | 1 |
| 27 OYL | 0 | 0 | 0 | 0 | 4 | 0 | 0 | 0 | 0 | 0 | 9 | 0 | 0 | 0 | 3 | 0 | 0 | 0 | 0 |
| 28 YBS | 2 | 0 | 5 | 1 | 0 | 0 | 0 | 1 | 0 | 0 | 0 | 1 | 0 | 0 | 1 | 2 | 3 | 0 | 0 |
| 29 OJI | 0 | 1 | 1 | 0 | 0 | 0 | 1 | 1 | 1 | 0 | 0 | 1 | 0 | 1 | 2 | 2 | 1 | 0 | 1 |
| 30 IJI | 1 | 4 | 4 | 1 | 3 | 1 | 2 | 0 | 0 | 1 | 2 | 1 | 2 | 0 | 3 | 0 | 0 | 1 | 2 |
| 31 YSJ | 1 | 1 | 1 | 1 | 1 | 0 | 1 | 1 | 2 | 1 | 0 | 0 | 1 | 1 | 1 | 1 | 0 | 1 | 1 |
| 32 LKS | 1 | 1 | 2 | 3 | 3 | 0 | 1 | 2 | 2 | 0 | 4 | 2 | 5 | 1 | 1 | 0 | 1 | 1 | 2 |
| 33 NXO | 1 | 0 | 2 | 1 | 1 | 1 | 1 | 0 | 0 | 1 | 1 | 1 | 1 | 1 | 2 | 0 | 1 | 0 | 1 |
| 34 UMS | 1 | 3 | 0 | 1 | 1 | 1 | 1 | 0 | 0 | 0 | 1 | 1 | 3 | 1 | 2 | 1 | 0 | 1 | 2 |
| 35 YOK | 1 | 2 | 1 | 2 | 3 | 0 | 1 | 1 | 2 | 0 | 1 | 2 | 3 | 3 | 1 | 2 | 2 | 0 | 1 |
| 36 AKJ | 2 | 2 | 2 | 2 | 2 | 1 | 1 | 1 | 1 | 2 | 1 | 0 | 0 | 1 | 2 | 1 | 2 | 1 | 1 |
| 37 PIH | 3 | 1 | 3 | 1 | 1 | 2 | 2 | 1 | 3 | 4 | 1 | 0 | 0 | 1 | 2 | 3 | 2 | 3 | 1 |
| 38 KYS | 3 | 2 | 5 | 3 | 3 | 1 | 0 | 1 | 2 | 2 | 1 | 0 | 3 | 3 | 2 | 1 | 3 | 1 | 1 |
| 39 JJM | 3 | 2 | 2 | 2 | 1 | 2 | 2 | 1 | 1 | 1 | 2 | 3 | 3 | 2 | 3 | 2 | 2 | 1 | 2 |
| 40 NMO | 4 | 2 | 4 | 3 | 3 | 2 | 1 | 1 | 3 | 3 | 4 | 2 | 1 | 1 | 1 | 2 | 2 | 1 | 2 |
| 41 SSS | 3 | 3 | 2 | 2 | 3 | 2 | 1 | 1 | 2 | 2 | 3 | 2 | 1 | 1 | 3 | 3 | 2 | 1 | 1 |
| 42 YKJ | 4 | 2 | 5 | 3 | 3 | 1 | 1 | 2 | 2 | 1 | 0 | 1 | 0 | 3 | 1 | 1 | 0 | 1 | 1 |
| 43 SJK | 0 | 0 | 1 | 5 | 0 | 1 | 0 | 0 | 1 | 2 | 3 | 2 | 3 | 1 | 0 | 1 | 1 | 1 | 0 |
| 44 IYS | 1 | 1 | 0 | 1 | 1 | 0 | 0 | 1 | 1 | 0 | 1 | 1 | 1 | 1 | 1 | 1 | 0 | 0 | 1 |
| 45 JJN | 3 | 2 | 3 | 2 | 2 | 2 | 3 | 3 | 1 | 1 | 0 | 1 | 2 | 2 | 3 | 1 | 1 | 2 | 3 |
| 46 MYJ | 4 | 4 | 4 | 0 | 4 | 3 | 3 | 4 | 4 | 3 | 1 | 1 | 2 | 3 | 2 | 3 | 2 | 1 | 3 |
| 47 NKS | 0 | 0 | 0 | 2 | 0 | 2 | 0 | 0 | 0 | 1 | 0 | 0 | 0 | 0 | 0 | 0 | 0 | 0 | 0 |
| 48 YOK | 1 | 0 | 2 | 0 | 0 | 0 | 0 | 0 | 0 | 0 | 2 | 0 | 0 | 2 | 2 | 1 | 0 | 1 | 0 |
| 49 HKS | 2 | 0 | 1 | 0 | 3 | 1 | 0 | 2 | 1 | 0 | 0 | 5 | 0 | 0 | 2 | 1 | 2 | 0 | 1 |
| 50 PJS | 0 | 0 | 0 | 0 | 0 | 0 | 0 | 0 | 2 | 0 | 1 | 1 | 0 | 0 | 0 | 0 | 0 | 0 | 1 |

Table 8 below shows the result of analyzing hTERT epitope screening using PBMCs obtained from a patient with lung cancer.

TABLE 8

| Patients | # Peptide 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| 1 BGO | 0 | 0 | 0 | 0 | 0 | 1 | 1 | 1 | 0 | 0 | 2 | 1 | 2 | 1 | 2 | 2 | 1 | 0 | 0 | 1 | 0 | 0 | 0 | 0 | 0 |
| 2 LCS | 1 | 0 | 0 | 0 | 0 | 0 | 0 | 1 | 0 | 0 | 1 | 1 | 0 | 0 | 0 | 0 | 4 | 0 | 1 | 0 | 0 | 0 | 1 | 0 | 0 |
| 3 KCH | 3 | 2 | 4 | 1 | 4 | 1 | 1 | 1 | 1 | 0 | 1 | 1 | 1 | 1 | 1 | 1 | 1 | 2 | 2 | 2 | 1 | 1 | 1 | 1 | 1 |
| 4 NSD | 1 | 2 | 4 | 1 | 2 | 3 | 2 | 2 | 1 | 2 | 2 | 2 | 2 | 2 | 2 | 3 | 2 | 2 | 1 | 1 | 2 | 1 | 2 | 1 | 1 |
| 5 CHS | 3 | 3 | 3 | 3 | 2 | 3 | 3 | 0 | 3 | 3 | 2 | 2 | 3 | 3 | 3 | 1 | 0 | 3 | 3 | 1 | 2 | 3 | 0 | 4 | 3 |
| 6 KCH | 1 | 0 | 2 | 2 | 0 | 0 | 0 | 0 | 1 | 2 | 0 | 0 | 1 | 0 | 0 | 0 | 0 | 0 | 0 | 0 | 1 | 0 | 1 | 0 | 0 |
| 7 CMR | 0 | 1 | 1 | 1 | 0 | 0 | 1 | 2 | 0 | 1 | 2 | 0 | 1 | 0 | 0 | 1 | 2 | 2 | 1 | 2 | 1 | 3 | 1 | 1 | 4 |
| 8 HJS | 0 | 0 | 1 | 0 | 2 | 2 | 2 | 1 | 2 | 0 | 0 | 1 | 0 | 0 | 0 | 0 | 0 | 2 | 0 | 0 | 0 | 0 | 0 | 0 | 0 |
| 9 PBS | 3 | 0 | 0 | 1 | 1 | 1 | 3 | 2 | 3 | 1 | 0 | 0 | 2 | 1 | 3 | 4 | 2 | 3 | 1 | 2 | 4 | 1 | 3 | 1 | 1 |
| 10 KSH | 5 | 3 | 2 | 1 | 2 | 1 | 2 | 2 | 4 | 3 | 1 | 1 | 1 | 1 | 1 | 3 | 4 | 1 | 3 | 1 | 2 | 3 | 0 | 3 | 3 |
| 11 LJS | 1 | 1 | 1 | 0 | 0 | 0 | 0 | 1 | 0 | 0 | 0 | 0 | 0 | 0 | 1 | 1 | 1 | 0 | 0 | 0 | 1 | 1 | 1 | 0 | 1 |
| 12 LKS | 1 | 1 | 3 | 2 | 3 | 2 | 1 | 1 | 2 | 2 | 0 | 1 | 1 | 2 | 1 | 5 | 0 | 2 | 2 | 3 | 3 | 1 | 3 | 4 | 2 |

TABLE 8-continued

| Patients | # Peptide 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| 13 LYS | 2 | 1 | 2 | 2 | 2 | 2 | 2 | 2 | 0 | 2 | 1 | 0 | 0 | 0 | 0 | 2 | 2 | 1 | 1 | 2 | 1 | 0 | 0 | 1 | 2 |
| 14 SMS | 0 | 0 | 1 | 0 | 1 | 0 | 1 | 2 | 0 | 5 | 0 | 1 | 1 | 0 | 2 | 3 | 2 | 2 | 0 | 0 | 2 | 0 | 2 | 0 | 1 |
| 15 KHS | 0 | 0 | 0 | 0 | 1 | 1 | 1 | 1 | 1 | 0 | 1 | 1 | 0 | 0 | 1 | 1 | 1 | 1 | 1 | 1 | 0 | 1 | 0 | 1 | 1 |
| 16 LKT | 0 | 1 | 2 | 1 | 0 | 0 | 2 | 0 | 0 | 2 | 2 | 2 | 0 | 2 | 2 | 1 | 0 | 0 | 1 | 1 | 0 | 0 | 0 | 0 | 0 |
| 17 EHR | 1 | 0 | 2 | 3 | 1 | 2 | 3 | 0 | 1 | 4 | 0 | 1 | 0 | 0 | 1 | 0 | 0 | 3 | 4 | 1 | 1 | 2 | 2 | 1 | 5 |
| 18 KYH | 4 | 3 | 4 | 4 | 4 | 4 | 4 | 2 | 3 | 5 | 1 | 3 | 1 | 4 | 3 | 2 | 2 | 3 | 3 | 1 | 1 | 1 | 1 | 3 | 2 |
| 19 CEH | 1 | 2 | 0 | 0 | 0 | 0 | 0 | 0 | 2 | 1 | 4 | 0 | 0 | 0 | 0 | 0 | 0 | 0 | 0 | 0 | 1 | 0 | 0 | 2 | 2 |
| 20 KSJ | 0 | 0 | 1 | 0 | 1 | 0 | 2 | 2 | 1 | 1 | 2 | 2 | 1 | 0 | 1 | 0 | 0 | 2 | 1 | 1 | 0 | 0 | 0 | 0 | 0 |

Table 9 below shows the result of analyzing hTERT epitope screening using PBMCs obtained from a patient with pancreatic cancer.

TABLE 9

| Patients | # Peptide 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| 1 KEH | 2 | 4 | 4 | 5 | 4 | 4 | 4 | 5 | 5 | 5 | 4 | 5 | 3 | 5 | 5 | 4 | 4 | 4 | 5 | 4 | 3 | 2 | 4 | 4 | 2 |
| 2 LSS | 1 | 2 | 1 | 1 | 1 | 2 | 2 | 0 | 0 | 1 | 2 | 1 | 1 | 1 | 1 | 0 | 2 | 1 | 1 | 1 | 1 | 2 | 1 | 1 | 1 |
| 3 KXS | 2 | 3 | 0 | 0 | 1 | 1 | 0 | 2 | 0 | 5 | 1 | 5 | 0 | 0 | 0 | 2 | 1 | 0 | 1 | 4 | 0 | 1 | 3 | 1 | 1 |
| 4 NSD | 1 | 1 | 1 | 1 | 1 | 1 | 2 | 1 | 1 | 1 | 1 | 1 | 2 | 2 | 0 | 2 | 1 | 1 | 1 | 1 | 1 | 1 | 2 | 1 | 1 |
| 5 JKK | 4 | 1 | 1 | 4 | 2 | 1 | 0 | 1 | 5 | 4 | 0 | 1 | 0 | 4 | 3 | 1 | 2 | 1 | 2 | 2 | 0 | 2 | 0 | 2 | 3 |
| 6 NIS | 1 | 1 | 1 | 1 | 1 | 1 | 1 | 1 | 1 | 2 | 2 | 1 | 2 | 2 | 5 | 1 | 1 | 0 | 0 | 0 | 1 | 1 | 1 | 0 | 0 |
| 7 PSN | 1 | 1 | 1 | 0 | 1 | 1 | 0 | 0 | 0 | 0 | 0 | 0 | 1 | 1 | 0 | 0 | 0 | 1 | 0 | 0 | 1 | 1 | 0 | 0 | 1 |
| 8 LJO | 1 | 1 | 1 | 1 | 0 | 0 | 0 | 1 | 1 | 1 | 1 | 2 | 1 | 1 | 3 | 2 | 4 | 0 | 0 | 1 | 2 | 0 | 0 | 0 | 2 |
| 9 SSW | 1 | 2 | 4 | 2 | 2 | 3 | 1 | 1 | 0 | 5 | 1 | 1 | 1 | 3 | 2 | 3 | 2 | 2 | 3 | 2 | 2 | 2 | 1 | 1 | 0 |
| 10 KSH | 0 | 0 | 1 | 2 | 1 | 1 | 2 | 3 | 2 | 1 | 1 | 1 | 0 | 2 | 2 | 0 | 2 | 1 | 1 | 1 | 0 | 1 | 1 | 2 | 2 |
| 11 JTJ | 1 | 1 | 1 | 0 | 1 | 1 | 2 | 1 | 2 | 3 | 0 | 1 | 1 | 0 | 0 | 5 | 1 | 0 | 1 | 1 | 0 | 1 | 0 | 4 | 2 |
| 12 KXH | 0 | 0 | 1 | 0 | 0 | 1 | 0 | 0 | 0 | 0 | 0 | 0 | 0 | 2 | 0 | 0 | 2 | 2 | 1 | 0 | 0 | 0 | 0 | 0 | 2 |
| 13 PSH | 5 | 1 | 1 | 0 | 0 | 1 | 0 | 1 | 1 | 3 | 1 | 0 | 0 | 0 | 0 | 2 | 1 | 1 | 0 | 2 | 1 | 0 | 0 | 1 | 0 |
| 14 LSB | 1 | 1 | 3 | 3 | 0 | 1 | 5 | 0 | 2 | 4 | 1 | 0 | 3 | 1 | 1 | 3 | 1 | 2 | 4 | 2 | 1 | 1 | 4 | 4 | 2 |
| 15 KMY | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 |
| 16 KCJ | 2 | 1 | 0 | 1 | 1 | 1 | 1 | 1 | 1 | 1 | 1 | 1 | 0 | 3 | 0 | 2 | 2 | 0 | 2 | 0 | 1 | 2 | 0 | 0 | 0 |
| 17 CSH | 2 | 1 | 3 | 4 | 4 | 4 | 3 | 2 | 2 | 2 | 1 | 1 | 3 | 3 | 3 | 4 | 3 | 2 | 2 | 2 | 2 | 2 | 1 | 2 | 1 |
| 18 CH | 4 | 4 | 3 | 5 | 4 | 5 | 4 | 4 | 5 | 5 | 1 | 4 | 4 | 5 | 4 | 2 | 3 | 3 | 3 | 4 | 4 | 4 | 3 | 4 | 4 |
| 19 HKS | 1 | 0 | 1 | 1 | 1 | 0 | 1 | 1 | 1 | 0 | 1 | 0 | 1 | 0 | 0 | 1 | 1 | 0 | 1 | 0 | 1 | 0 | 1 | 1 | 1 |
| 20 YSC | 1 | 1 | 0 | 2 | 0 | 0 | 0 | 0 | 1 | 3 | 0 | 0 | 1 | 0 | 0 | 1 | 0 | 1 | 0 | 1 | 1 | 1 | 1 | 1 | 1 |

Table 10 below shows the result of analyzing WT1 epitope screening using PBMCs obtained from a patient with glioblastoma.

TABLE 10

| Patients | # Peptide 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 1 KSK | 3 | 5 | 5 | 2 | 2 | 4 | 5 | 5 | 5 | 2 | 2 | 3 | 0 | 3 | 5 | 2 | 5 | 4 | 5 | 5 |
| 2 DSY | 3 | 1 | 1 | 2 | 2 | 1 | 0 | 2 | 0 | 1 | 0 | 0 | 1 | 3 | 1 | 3 | 2 | 2 | 2 | 1 |
| 3 JJY | 3 | 1 | 1 | 1 | 1 | 1 | 1 | 1 | 5 | 3 | 2 | 2 | 2 | 2 | 2 | 2 | 2 | 2 | 3 | 1 |
| 4 OJH | 3 | 3 | 2 | 2 | 2 | 2 | 1 | 4 | 3 | 1 | 2 | 2 | 3 | 1 | 1 | 3 | 3 | 2 | 5 | 3 |
| 5 KYA | 0 | 0 | 1 | 1 | 0 | 1 | 1 | 1 | 3 | 1 | 0 | 0 | 0 | 0 | 1 | 0 | 0 | 1 | 1 | 0 |
| 6 YSB | 0 | 0 | 0 | 2 | 1 | 0 | 0 | 0 | 0 | 5 | 5 | 0 | 3 | 0 | 1 | 0 | 0 | 0 | 0 | 1 |
| 7 KXJ | 1 | 1 | 2 | 1 | 1 | 2 | 1 | 1 | 1 | 1 | 1 | 2 | 2 | 2 | 1 | 2 | 2 | 1 | 2 | 1 |
| 8 NKH | 2 | 3 | 1 | 2 | 3 | 2 | 2 | 3 | 2 | 2 | 1 | 1 | 1 | 3 | 3 | 4 | 4 | 2 | 2 | 3 |
| 9 AKM | 0 | 0 | 0 | 0 | 1 | 1 | 0 | 2 | 1 | 0 | 0 | 1 | 1 | 0 | 1 | 1 | 0 | 1 | 1 | 0 |
| 10 HIS | 1 | 1 | 0 | 1 | 1 | 1 | 0 | 1 | 1 | 1 | 1 | 0 | 0 | 1 | 0 | 0 | 0 | 0 | 0 | 1 |
| 11 CHY | 4 | 3 | 4 | 3 | 2 | 3 | 2 | 4 | 5 | 4 | 3 | 2 | 2 | 3 | 2 | 3 | 2 | 3 | 3 | 3 |
| 12 JYS | 3 | 4 | 2 | 2 | 4 | 5 | 2 | 4 | 4 | 4 | 2 | 3 | 2 | 3 | 3 | 4 | 4 | 2 | 3 | 3 |
| 13 HIS | 2 | 1 | 1 | 1 | 1 | 0 | 1 | 1 | 1 | 2 | 0 | 0 | 1 | 0 | 1 | 0 | 0 | 1 | 0 | 2 |
| 14 ABS | 2 | 2 | 2 | 1 | 4 | 1 | 1 | 4 | 3 | 3 | 4 | 1 | 1 | 1 | 2 | 4 | 2 | 2 | 2 | 2 |
| 15 LYJ | 3 | 2 | 2 | 2 | 2 | 0 | 1 | 2 | 1 | 2 | 3 | 1 | 1 | 3 | 0 | 1 | 1 | 1 | 3 | 0 |
| 16 SBS | 1 | 2 | 0 | 0 | 1 | 1 | 0 | 1 | 2 | 1 | 0 | 0 | 0 | 2 | 2 | 1 | 2 | 2 | 1 | 1 |
| 17 PJB | 2 | 2 | 2 | 1 | 4 | 2 | 1 | 1 | 1 | 1 | 1 | 1 | 1 | 1 | 1 | 3 | 1 | 1 | 1 | 1 |
| 18 JJS | 5 | 5 | 5 | 5 | 5 | 5 | 5 | 5 | 5 | 5 | 5 | 5 | 5 | 5 | 5 | 5 | 5 | 5 | 5 | 5 |
| 19 LVH | 1 | 0 | 0 | 0 | 0 | 0 | 0 | 0 | 0 | 0 | 0 | 0 | 0 | 1 | 0 | 0 | 0 | 0 | 1 | 1 |
| 20 SSO | 0 | 0 | 0 | 0 | 0 | 0 | 0 | 0 | 0 | 0 | 0 | 0 | 0 | 0 | 0 | 0 | 0 | 0 | 0 | 0 |

Table 11 below shows the result of analyzing WT1 epitope screening using PBMCs obtained from a patient with lung cancer.

TABLE 11

| | # Peptide | | | | | | | | | | | | | | | | | | | |
|---|---|---|---|---|---|---|---|---|---|---|---|---|---|---|---|---|---|---|---|---|
| Patients | 1 | 2 | 3 | 4 | 5 | 6 | 7 | 8 | 9 | 10 | 11 | 12 | 13 | 14 | 15 | 16 | 17 | 18 | 19 | 20 |
| 1 BGO | 2 | 1 | 0 | 0 | 1 | 0 | 2 | 2 | 3 | 1 | 1 | 1 | 0 | 0 | 2 | 1 | 1 | 1 | 1 | 1 |
| 2 LCS | 1 | 0 | 0 | 1 | 0 | 0 | 0 | 0 | 0 | 1 | 1 | 0 | 1 | 0 | 0 | 0 | 0 | 1 | 0 | 0 |
| 3 KOH | 0 | 1 | 1 | 2 | 2 | 0 | 2 | 2 | 4 | 5 | 2 | 1 | 1 | 1 | 1 | 1 | 3 | 1 | 2 | 1 |
| 4 NSD | 2 | 1 | 2 | 1 | 2 | 1 | 1 | 2 | 2 | 1 | 2 | 3 | 3 | 3 | 3 | 2 | 3 | 1 | 1 | 1 |
| 5 CHS | 3 | 4 | 3 | 3 | 3 | 3 | 3 | 3 | 0 | 2 | 2 | 1 | 4 | 4 | 3 | 5 | 3 | 1 | 4 | 3 |
| 6 KCH | 0 | 0 | 1 | 1 | 2 | 2 | 1 | 1 | 1 | 1 | 1 | 0 | 0 | 0 | 0 | 0 | 0 | 1 | 0 | 2 |
| 7 CMR | 2 | 0 | 2 | 2 | 1 | 3 | 0 | 0 | 0 | 1 | 0 | 0 | 3 | 0 | 0 | 0 | 1 | 0 | 0 | 0 |
| 8 HJS | 0 | 0 | 0 | 1 | 1 | 2 | 1 | 1 | 1 | 4 | 0 | 0 | 0 | 1 | 0 | 1 | 0 | 0 | 0 | 3 |
| 9 PBS | 0 | 2 | 0 | 2 | 0 | 0 | 0 | 2 | 0 | 0 | 2 | 3 | 3 | 1 | 3 | 2 | 3 | 1 | 1 | 3 |
| 10 KSH | 3 | 3 | 3 | 3 | 3 | 1 | 3 | 3 | 4 | 3 | 2 | 2 | 1 | 1 | 2 | 3 | 3 | 3 | 3 | 3 |
| 11 LJS | 1 | 1 | 1 | 1 | 0 | 0 | 1 | 1 | 1 | 0 | 1 | 1 | 0 | 0 | 0 | 0 | 0 | 1 | 1 | 1 |
| 12 LKS | 2 | 2 | 2 | 1 | 3 | 3 | 2 | 1 | 2 | 0 | 2 | 2 | 2 | 4 | 4 | 1 | 0 | 4 | 2 | 0 |
| 13 LYS | 0 | 3 | 2 | 0 | 1 | 1 | 3 | 0 | 1 | 1 | 1 | 1 | 0 | 0 | 0 | 1 | 0 | 0 | 1 | 1 |
| 14 SMS | 2 | 1 | 1 | 2 | 1 | 1 | 1 | 1 | 4 | 0 | 1 | 0 | 1 | 1 | 1 | 1 | 1 | 1 | 1 | 1 |
| 15 KHS | 1 | 1 | 1 | 0 | 0 | 1 | 0 | 1 | 1 | 1 | 1 | 1 | 1 | 1 | 0 | 1 | 1 | 1 | 1 | 1 |
| 16 LKT | 2 | 0 | 0 | 0 | 0 | 1 | 0 | 1 | 0 | 1 | 0 | 0 | 2 | 1 | 1 | 0 | 0 | 5 | 1 | 0 |
| 17 EHR | 2 | 1 | 0 | 3 | 2 | 1 | 1 | 1 | 3 | 1 | 4 | 2 | 1 | 2 | 1 | 1 | 3 | 0 | 3 | 2 |
| 18 KYH | 4 | 3 | 3 | 3 | 3 | 4 | 3 | 3 | 3 | 3 | 1 | 1 | 1 | 2 | 3 | 2 | 2 | 1 | 1 | 3 |
| 19 CEH | 0 | 1 | 2 | 0 | 0 | 0 | 0 | 0 | 2 | 0 | 0 | 0 | 0 | 0 | 0 | 1 | 0 | 0 | 0 | 2 |
| 20 KSJ | 2 | 1 | 1 | 2 | 1 | 0 | 3 | 1 | 1 | 5 | 3 | 0 | 0 | 1 | 2 | 1 | 1 | 0 | 1 | 1 |

Table 12 below shows the result of analyzing NY-ESO1 epitope screening using PBMCs obtained from a patient with ovarian cancer.

TABLE 12

| | # Peptide | | | | | | | | | | | | | | | | | | | |
|---|---|---|---|---|---|---|---|---|---|---|---|---|---|---|---|---|---|---|---|---|
| Patients | 1 | 2 | 3 | 4 | 5 | 6 | 7 | 8 | 9 | 10 | 11 | 12 | 13 | 14 | 15 | 16 | 17 | 18 | 19 | 20 |
| 1 CEH | 0 | 0 | 0 | 1 | 0 | 0 | 2 | 1 | 2 | 0 | 2 | 2 | 0 | 1 | 1 | 0 | 0 | 2 | 1 | 0 |
| 2 LBS | 1 | 1 | 0 | 1 | 1 | 0 | 0 | 1 | 1 | 0 | 0 | 1 | 0 | 1 | 0 | 0 | 1 | 2 | 0 | 0 |
| 3 KSY | 1 | 0 | 3 | 2 | 3 | 1 | 1 | 2 | 0 | 2 | 1 | 2 | 1 | 1 | 0 | 1 | 1 | 0 | 0 | 1 |
| 4 KMS | 1 | 1 | 1 | 2 | 2 | 3 | 4 | 2 | 4 | 1 | 5 | 1 | 1 | 3 | 1 | 2 | 4 | 3 | 1 | 1 |
| 5 HSY | 0 | 0 | 0 | 0 | 0 | 0 | 0 | 0 | 2 | 2 | 0 | 0 | 1 | 0 | 0 | 0 | 0 | 1 | 0 | 3 |
| 6 KHJ | 1 | 2 | 3 | 1 | 1 | 1 | 2 | 1 | 1 | 3 | 3 | 1 | 2 | 2 | 3 | 1 | 1 | 1 | 1 | 2 |
| 7 LKS | 1 | 0 | 5 | 1 | 1 | 1 | 1 | 1 | 1 | 5 | 3 | 2 | 1 | 1 | 4 | 1 | 1 | 1 | 5 | 1 |
| 8 KHM | 1 | 1 | 5 | 3 | 0 | 1 | 2 | 0 | 2 | 1 | 1 | 0 | 0 | 2 | 0 | 1 | 1 | 1 | 0 | 3 |
| 9 JMJ | 2 | 1 | 1 | 2 | 0 | 0 | 0 | 1 | 1 | 1 | 1 | 0 | 1 | 0 | 0 | 0 | 0 | 1 | 1 | 0 |
| 10 YSG | 1 | 0 | 1 | 1 | 1 | 0 | 0 | 0 | 1 | 1 | 0 | 1 | 1 | 1 | 1 | 0 | 0 | 1 | 1 | 0 |
| 11 KMH | 1 | 0 | 2 | 2 | 0 | 2 | 0 | 2 | 1 | 2 | 0 | 2 | 1 | 1 | 1 | 2 | 0 | 2 | 2 | 2 |
| 12 JYS | 3 | 3 | 2 | 3 | 2 | 4 | 2 | 2 | 3 | 1 | 3 | 2 | 2 | 1 | 1 | 4 | 2 | 2 | 2 | 2 |
| 13 PJS | 0 | 0 | 1 | 0 | 1 | 0 | 2 | 1 | 2 | 1 | 1 | 0 | 0 | 1 | 1 | 0 | 3 | 0 | 0 | 0 |
| 14 SSS | 0 | 2 | 1 | 2 | 2 | 3 | 1 | 0 | 0 | 0 | 0 | 0 | 0 | 2 | 0 | 0 | 1 | 1 | 0 | 0 |
| 15 HYH | 0 | 2 | 0 | 2 | 0 | 1 | 2 | 0 | 2 | 2 | 0 | 0 | 0 | 0 | 1 | 1 | 0 | 1 | 2 | 0 |
| 16 KMS | 3 | 3 | 3 | 3 | 5 | 5 | 4 | 4 | 3 | 3 | 5 | 5 | 2 | 2 | 4 | 3 | 3 | 2 | 4 | 4 |
| 17 KYS | 0 | 1 | 5 | 3 | 1 | 0 | 1 | 2 | 0 | 2 | 1 | 2 | 0 | 2 | 0 | 4 | 0 | 1 | 2 | 2 |
| 18 YEK | 1 | 1 | 2 | 0 | 0 | 3 | 0 | 5 | 2 | 1 | 1 | 2 | 3 | 4 | 0 | 2 | 0 | 4 | 0 | 5 |
| 19 LYJ | 1 | 1 | 2 | 2 | 1 | 2 | 2 | 2 | 1 | 2 | 1 | 0 | 1 | 1 | 0 | 1 | 0 | 2 | 1 | 1 |
| 20 KKS | 0 | 1 | 0 | 0 | 0 | 1 | 0 | 0 | 2 | 3 | 1 | 0 | 0 | 0 | 1 | 2 | 2 | 2 | 1 | 3 |
| 21 HHS | 0 | 0 | 1 | 0 | 0 | 2 | 2 | 0 | 1 | 0 | 0 | 0 | 0 | 1 | 2 | 1 | 1 | 1 | 0 | 0 |
| 22 LKS | 1 | 2 | 4 | 2 | 0 | 1 | 2 | 1 | 1 | 1 | 2 | 0 | 2 | 2 | 0 | 1 | 2 | 1 | 0 | 1 |
| 23 PSD | 0 | 0 | 0 | 1 | 0 | 1 | 1 | 0 | 0 | 0 | 0 | 0 | 0 | 0 | 0 | 0 | 0 | 0 | 0 | 0 |
| 24 SES | 3 | 1 | 0 | 0 | 0 | 0 | 1 | 2 | 2 | 1 | 2 | 0 | 1 | 0 | 0 | 0 | 2 | 0 | 0 | 0 |
| 25 JHY | 2 | 1 | 2 | 1 | 1 | 2 | 2 | 1 | 2 | 2 | 2 | 2 | 1 | 1 | 2 | 2 | 2 | 1 | 1 | 1 |
| 26 KKH | 1 | 0 | 1 | 3 | 3 | 4 | 0 | 1 | 3 | 2 | 3 | 1 | 1 | 2 | 2 | 1 | 3 | 3 | 4 | 2 |
| 27 KYJ | 2 | 2 | 2 | 3 | 2 | 2 | 1 | 2 | 1 | 2 | 2 | 2 | 1 | 1 | 0 | 1 | 1 | 2 | 0 | 0 |
| 28 KGH | 5 | 5 | 5 | 4 | 4 | 5 | 5 | 4 | 5 | 4 | 4 | 5 | 4 | 4 | 4 | 5 | 4 | 5 | 5 | 4 |
| 29 KSK | 1 | 1 | 4 | 1 | 3 | 1 | 1 | 1 | 2 | 3 | 3 | 1 | 2 | 2 | 2 | 1 | 1 | 2 | 0 | 1 |
| 30 SJH | 5 | 2 | 1 | 3 | 2 | 5 | 4 | 4 | 3 | 0 | 4 | 1 | 3 | 2 | 1 | 4 | 2 | 2 | 5 | 2 |

Table 13 below shows the result of analyzing WT1 epitope screening using PBMCs obtained from a patient with sarcoma.

TABLE 13

| Patients | # Peptide 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 1 LVS | 1 | 3 | 5 | 1 | 1 | 1 | 1 | 2 | 1 | 1 | 1 | 1 | 2 | 1 | 1 | 2 | 2 | 2 | 1 | 1 |
| 2 SJV | 3 | 3 | 3 | 4 | 5 | 1 | 0 | 3 | 1 | 1 | 1 | 1 | 3 | 2 | 1 | 3 | 4 | 4 | 1 | 1 |
| 3 AVS | 1 | 1 | 2 | 2 | 3 | 1 | 2 | 1 | 2 | 4 | 2 | 2 | 1 | 1 | 2 | 1 | 2 | 3 | 1 | 1 |
| 4 KDS | 1 | 1 | 1 | 1 | 1 | 1 | 1 | 1 | 1 | 1 | 1 | 1 | 1 | 1 | 2 | 1 | 3 | 3 | 1 | 1 |
| 5 LSM | 0 | 0 | 0 | 1 | 0 | 0 | 0 | 0 | 0 | 0 | 0 | 0 | 0 | 0 | 0 | 0 | 0 | 0 | 2 | 0 |
| 6 CSK | 0 | 2 | 1 | 1 | 1 | 0 | 0 | 0 | 0 | 1 | 0 | 0 | 0 | 1 | 1 | 1 | 2 | 1 | 0 | 2 |
| 7 JJS | 2 | 1 | 0 | 2 | 4 | 3 | 1 | 2 | 2 | 1 | 3 | 0 | 4 | 2 | 2 | 0 | 2 | 1 | 1 | 0 |
| 8 PVS | 1 | 1 | 3 | 2 | 0 | 0 | 2 | 1 | 1 | 1 | 0 | 1 | 1 | 1 | 1 | 1 | 0 | 1 | 0 | 0 |
| 9 LVS | 1 | 2 | 5 | 1 | 1 | 1 | 1 | 1 | 3 | 2 | 1 | 4 | 1 | 0 | 2 | 3 | 1 | 1 | 2 | 0 |
| 10 KYS | 0 | 0 | 0 | 0 | 0 | 0 | 0 | 0 | 0 | 0 | 0 | 0 | 0 | 0 | 0 | 0 | 0 | 0 | 0 | 0 |
| 11 YJH | 0 | 0 | 0 | 0 | 0 | 0 | 0 | 0 | 0 | 0 | 0 | 0 | 3 | 0 | 0 | 0 | 0 | 0 | 0 | 0 |
| 12 KVC | 1 | 2 | 0 | 1 | 1 | 0 | 0 | 0 | 0 | 3 | 0 | 1 | 0 | 0 | 0 | 1 | 1 | 1 | 1 | 0 |
| 13 LSH | 1 | 2 | 1 | 1 | 0 | 0 | 1 | 1 | 1 | 0 | 0 | 0 | 0 | 0 | 1 | 2 | 1 | 0 | 0 | 0 |
| 14 ESJ | 0 | 1 | 1 | 1 | 1 | 0 | 0 | 0 | 0 | 0 | 0 | 0 | 1 | 0 | 0 | 0 | 0 | 0 | 1 | 0 |
| 15 HSH | 0 | 0 | 2 | 0 | 0 | 0 | 0 | 1 | 0 | 0 | 0 | 0 | 0 | 0 | 1 | 0 | 0 | 0 | 0 | 0 |
| 16 PCI | 0 | 0 | 0 | 0 | 0 | 0 | 0 | 0 | 0 | 0 | 0 | 0 | 0 | 0 | 0 | 0 | 0 | 0 | 0 | 0 |
| 17 KJS | 2 | 2 | 5 | 2 | 2 | 0 | 1 | 1 | 1 | 3 | 0 | 0 | 1 | 0 | 2 | 2 | 1 | 1 | 2 | 2 |
| 18 JBK | 1 | 1 | 1 | 0 | 1 | 0 | 1 | 0 | 1 | 1 | 1 | 1 | 3 | 1 | 1 | 1 | 0 | 1 | 0 | 1 |
| 19 CVR | 2 | 0 | 2 | 1 | 1 | 2 | 0 | 1 | 1 | 3 | 2 | 1 | 0 | 1 | 0 | 5 | 2 | 3 | 0 | 0 |
| 20 KNY | 0 | 1 | 0 | 1 | 1 | 2 | 1 | 0 | 2 | 0 | 1 | 1 | 0 | 0 | 1 | 1 | 0 | 2 | 2 | 1 |
| 21 KKC | 4 | 3 | 2 | 3 | 3 | 3 | 5 | 5 | 5 | 4 | 3 | 2 | 5 | 3 | 5 | 2 | 5 | 4 | 3 | 2 |
| 22 KMS | 1 | 0 | 5 | 5 | 3 | 5 | 2 | 2 | 1 | 1 | 3 | 3 | 0 | 0 | 3 | 0 | 0 | 3 | 2 | 1 |
| 23 KJM | 1 | 1 | 5 | 1 | 2 | 1 | 1 | 1 | 0 | 3 | 0 | 2 | 0 | 0 | 1 | 1 | 0 | 1 | 1 | 0 |
| 24 LMJ | 0 | 0 | 2 | 0 | 0 | 0 | 0 | 0 | 0 | 0 | 0 | 0 | 0 | 0 | 0 | 0 | 0 | 0 | 0 | 0 |
| 25 PHS | 0 | 0 | 2 | 4 | 2 | 5 | 1 | 3 | 2 | 3 | 1 | 1 | 2 | 1 | 5 | 2 | 2 | 1 | 1 | 4 |
| 26 YSH | 2 | 1 | 2 | 2 | 1 | 1 | 1 | 1 | 3 | 5 | 2 | 2 | 0 | 1 | 1 | 2 | 1 | 2 | 1 | 1 |
| 27 HSW | 0 | 3 | 5 | 1 | 2 | 1 | 3 | 0 | 3 | 2 | 1 | 2 | 0 | 2 | 0 | 0 | 1 | 1 | 0 | 1 |
| 28 SSB | 1 | 0 | 1 | 2 | 2 | 2 | 2 | 2 | 3 | 1 | 1 | 2 | 1 | 2 | 1 | 1 | 2 | 1 | 2 | 2 |
| 29 JSH | 0 | 0 | 0 | 0 | 0 | 0 | 1 | 1 | 1 | 1 | 0 | 0 | 0 | 0 | 1 | 1 | 0 | 0 | 2 | 1 |
| 30 RCH | 2 | 3 | 2 | 2 | 1 | 2 | 3 | 1 | 3 | 1 | 3 | 1 | 2 | 4 | 1 | 2 | 1 | 1 | 1 | 3 |

Table 14 below shows the result of analyzing MAGE-A3 epitope screening using PBMCs obtained from a patient with sarcoma.

Table 15 below shows the result of analyzing MAGE-A3 epitope screening using PBMCs obtained from a patient with lung cancer.

TABLE 14

| Patients | # Peptide 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| 1 LVS | 1 | 2 | 1 | 0 | 1 | 1 | 1 | 1 | 2 | 1 | 1 | 0 | 1 | 1 | 1 | 1 | 0 | 2 | 2 | 2 | 2 | 1 | 1 | 1 |
| 2 SJV | 3 | 1 | 0 | 2 | 3 | 3 | 0 | 2 | 1 | 1 | 2 | 3 | 2 | 4 | 3 | 5 | 0 | 0 | 1 | 1 | 4 | 4 | 1 | 1 |
| 3 AVS | 1 | 2 | 3 | 2 | 1 | 1 | 1 | 3 | 2 | 2 | 1 | 0 | 3 | 2 | 2 | 2 | 3 | 4 | 2 | 1 | 2 | 3 | 2 | 1 |
| 4 KDS | 0 | 1 | 1 | 1 | 1 | 2 | 2 | 2 | 1 | 0 | 1 | 0 | 3 | 1 | 2 | 1 | 1 | 0 | 1 | 1 | 0 | 1 | 2 | 5 |
| 5 LSM | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 6 CSK | 2 | 0 | 1 | 0 | 0 | 0 | 0 | 0 | 1 | 1 | 0 | 0 | 0 | 1 | 0 | 3 | 0 | 0 | 1 | 1 | 1 | 0 | 1 | 1 |
| 7 JJS | 1 | 0 | 2 | 1 | 0 | 3 | 3 | 0 | 4 | 3 | 0 | 3 | 1 | 1 | 2 | 2 | 0 | 2 | 0 | 2 | 0 | 0 | 1 | 1 |
| 8 PYS | 1 | 1 | 0 | 1 | 1 | 1 | 1 | 0 | 1 | 2 | 1 | 0 | 2 | 0 | 0 | 0 | 0 | 0 | 2 | 1 | 2 | 1 | 0 | 0 |
| 9 LYS | 5 | 1 | 4 | 0 | 1 | 2 | 0 | 1 | 1 | 1 | 1 | 1 | 0 | 0 | 0 | 0 | 1 | 1 | 3 | 1 | 0 | 0 | 1 | 1 |
| 10 KYS | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 11 YJH | 0 | 1 | 2 | 0 | 0 | 0 | 0 | 0 | 1 | 0 | 2 | 0 | 0 | 0 | 0 | 0 | 0 | 0 | 0 | 0 | 0 | 0 | 0 | 0 |
| 12 KYC | 2 | 1 | 0 | 0 | 0 | 1 | 0 | 1 | 0 | 0 | 0 | 0 | 0 | 0 | 0 | 0 | 0 | 2 | 0 | 0 | 2 | 0 | 0 | 0 |
| 13 LSH | 0 | 0 | 0 | 1 | 0 | 1 | 0 | 0 | 1 | 0 | 1 | 3 | 0 | 2 | 0 | 0 | 1 | 1 | 1 | 2 | 2 | 0 | 0 | 0 |
| 14 ESJ | 0 | 0 | 0 | 1 | 0 | 1 | 0 | 0 | 1 | 0 | 0 | 0 | 0 | 0 | 0 | 0 | 0 | 0 | 1 | 0 | 0 | 0 | 0 | 0 |
| 15 MBH | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 16 PCI | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 17 KJS | 2 | 2 | 2 | 1 | 1 | 0 | 0 | 1 | 2 | 2 | 1 | 3 | 0 | 2 | 2 | 0 | 1 | 1 | 1 | 1 | 0 | 2 | 1 | 0 |
| 18 JBK | 1 | 0 | 0 | 1 | 0 | 0 | 0 | 0 | 1 | 0 | 1 | 1 | 0 | 1 | 0 | 0 | 1 | 1 | 1 | 0 | 1 | 1 | 1 | 0 |
| 19 CYR | 0 | 1 | 1 | 0 | 2 | 0 | 1 | 1 | 1 | 0 | 5 | 0 | 5 | 1 | 2 | 2 | 0 | 0 | 3 | 0 | 2 | 0 | 2 | 1 |
| 20 KNY | 1 | 1 | 1 | 2 | 2 | 2 | 2 | 1 | 1 | 1 | 2 | 0 | 1 | 1 | 1 | 3 | 0 | 0 | 2 | 1 | 1 | 3 | 0 | 1 |
| 21 KXC | 2 | 2 | 5 | 4 | 3 | 4 | 4 | 3 | 4 | 3 | 1 | 3 | 1 | 4 | 3 | 2 | 4 | 4 | 4 | 5 | 2 | 3 | 3 | 3 |
| 22 KMS | 1 | 1 | 2 | 1 | 0 | 2 | 1 | 3 | 1 | 1 | 0 | 2 | 2 | 0 | 1 | 1 | 1 | 1 | 2 | 1 | 2 | 1 | 5 | 5 |
| 23 KJM | 1 | 0 | 1 | 1 | 1 | 1 | 0 | 0 | 0 | 1 | 0 | 0 | 0 | 0 | 1 | 0 | 0 | 0 | 1 | 0 | 1 | 1 | 1 | 1 |
| 24 LMJ | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 25 PHS | 1 | 1 | 2 | 1 | 0 | 1 | 4 | 3 | 0 | 4 | 0 | 1 | 0 | 2 | 1 | 0 | 0 | 1 | 1 | 2 | 1 | 2 | 4 | 2 |
| 26 YSH | 0 | 1 | 1 | 2 | 1 | 3 | 1 | 1 | 2 | 0 | 3 | 3 | 1 | 1 | 2 | 1 | 1 | 1 | 3 | 0 | 0 | 1 | 1 | 1 |
| 27 HSW | 0 | 1 | 1 | 1 | 1 | 1 | 3 | 1 | 0 | 3 | 2 | 0 | 2 | 1 | 0 | 0 | 1 | 0 | 0 | 1 | 2 | 4 | 0 | 1 |
| 28 SSB | 2 | 1 | 2 | 2 | 2 | 2 | 3 | 2 | 0 | 1 | 2 | 0 | 3 | 0 | 2 | 1 | 0 | 2 | 0 | 2 | 0 | 0 | 0 | 3 |
| 29 JSH | 1 | 0 | 0 | 0 | 0 | 0 | 1 | 1 | 0 | 0 | 1 | 0 | 1 | 0 | 1 | 2 | 0 | 0 | 0 | 0 | 0 | 0 | 0 | 0 |
| 30 RCH | 1 | 1 | 1 | 1 | 2 | 1 | 1 | 3 | 1 | 3 | 3 | 1 | 2 | 1 | 1 | 1 | 2 | 1 | 3 | 2 | 2 | 1 | 2 | 1 |

TABLE 15

| Patients | # Peptide | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| 1 BGO | 2 | 1 | 3 | 1 | 1 | 4 | 1 | 1 | 1 | 1 | 2 | 2 | 2 | 1 | 1 | 1 | 1 | 1 | 2 | 1 | 2 | 3 | 0 | 1 |
| 2 LCS | 0 | 0 | 0 | 0 | 0 | 0 | 1 | 1 | 2 | 0 | 0 | 0 | 0 | 0 | 0 | 0 | 0 | 0 | 0 | 0 | 0 | 0 | 1 | 1 |
| 3 KXH | 1 | 1 | 1 | 1 | 3 | 1 | 1 | 5 | 5 | 5 | 1 | 1 | 1 | 1 | 1 | 1 | 1 | 1 | 5 | 1 | 5 | 1 | 1 | 1 |
| 4 NSD | 1 | 1 | 2 | 2 | 2 | 1 | 1 | 2 | 2 | 2 | 2 | 1 | 1 | 3 | 0 | 4 | 0 | 2 | 3 | 1 | 1 | 2 | 1 | 1 |
| 5 CHS | 3 | 2 | 3 | 3 | 4 | 4 | 3 | 2 | 3 | 3 | 2 | 3 | 3 | 3 | 3 | 4 | 4 | 3 | 0 | 2 | 1 | 2 | 2 | 1 |
| 6 KCH | 0 | 0 | 0 | 0 | 2 | 1 | 1 | 1 | 0 | 2 | 0 | 1 | 0 | 0 | 2 | 0 | 0 | 0 | 0 | 2 | 0 | 0 | 1 | 1 |
| 7 CMR | 0 | 0 | 2 | 0 | 4 | 0 | 0 | 0 | 0 | 2 | 0 | 0 | 3 | 2 | 2 | 0 | 0 | 0 | 2 | 0 | 0 | 0 | 0 | 2 |
| 8 HJS | 0 | 0 | 2 | 0 | 1 | 0 | 0 | 2 | 1 | 0 | 0 | 2 | 1 | 1 | 1 | 1 | 1 | 2 | 0 | 0 | 0 | 0 | 3 | 2 |
| 9 PBS | 0 | 4 | 2 | 3 | 2 | 1 | 2 | 4 | 1 | 1 | 0 | 4 | 1 | 2 | 2 | 0 | 1 | 1 | 2 | 3 | 2 | 0 | 0 | 2 |
| 10 KSH | 2 | 3 | 1 | 1 | 2 | 2 | 2 | 3 | 1 | 3 | 1 | 2 | 1 | 2 | 2 | 2 | 2 | 3 | 3 | 1 | 3 | 2 | 2 | 3 |
| 11 LJS | 1 | 1 | 1 | 1 | 1 | 0 | 1 | 1 | 1 | 0 | 1 | 0 | 1 | 1 | 0 | 1 | 0 | 0 | 1 | 0 | 0 | 0 | 0 | 0 |
| 12 LKS | 5 | 5 | 2 | 0 | 2 | 2 | 1 | 5 | 4 | 1 | 1 | 0 | 4 | 1 | 0 | 2 | 1 | 1 | 2 | 2 | 0 | 2 | 2 | 2 |
| 13 LYS | 1 | 4 | 0 | 1 | 0 | 2 | 1 | 0 | 2 | 0 | 2 | 2 | 0 | 0 | 0 | 2 | 2 | 5 | 0 | 2 | 1 | 1 | 1 | 1 |
| 14 SMS | 1 | 2 | 2 | 2 | 0 | 2 | 1 | 0 | 2 | 0 | 1 | 1 | 2 | 1 | 1 | 0 | 2 | 1 | 0 | 1 | 2 | 1 | 0 | 3 |
| 15 KHS | 0 | 1 | 1 | 1 | 1 | 1 | 1 | 1 | 2 | 0 | 0 | 1 | 1 | 1 | 1 | 1 | 0 | 1 | 1 | 0 | 1 | 0 | 1 | 0 |
| 16 LKT | 1 | 0 | 0 | 0 | 2 | 0 | 2 | 2 | 1 | 1 | 2 | 0 | 0 | 1 | 2 | 2 | 1 | 1 | 0 | 2 | 1 | 1 | 1 | 1 |
| 17 EHR | 3 | 1 | 2 | 1 | 1 | 1 | 1 | 4 | 0 | 0 | 1 | 1 | 3 | 1 | 3 | 2 | 2 | 0 | 0 | 0 | 1 | 3 | 1 | 3 |
| 18 KYH | 1 | 4 | 3 | 2 | 2 | 2 | 3 | 2 | 1 | 3 | 1 | 2 | 3 | 2 | 2 | 2 | 2 | 2 | 1 | 3 | 2 | 3 | 3 | 2 |
| 19 CEH | 0 | 0 | 2 | 2 | 0 | 0 | 0 | 0 | 0 | 0 | 2 | 3 | 0 | 1 | 0 | 0 | 0 | 0 | 2 | 0 | 0 | 0 | 0 | 0 |
| 20 KSJ | 2 | 1 | 1 | 0 | 0 | 0 | 0 | 2 | 0 | 2 | 0 | 1 | 2 | 1 | 2 | 0 | 0 | 0 | 0 | 3 | 2 | 2 | 3 | 2 |

As shown in Tables 7 to 13, when CD8 T cells express 4-1 BB with at least score 3 by peptide stimulation, these cells can be effectively isolated by using an anti-4-1BB antibody. For each type of cancer, since the ratio of T cell responsive to the autologous cancer antigen with at least score 3 was in a degree of 40 to 50%, it has been determined that a T cell therapeutic agent can be prepared by using the selected epitopes of the autologous cancer antigen. The selected peptides are as follows: hTERT peptide: CLKELVARV (SEQ ID NO: 1), PLFLELL (SEQ ID NO: 2), AAVTPAA (SEQ ID NO: 3); WT1 peptide: SLGEQQVSV (SEQ ID NO: 4), RMFPNAPVL (SEQ ID NO: 5), CMTWNQMNL (SEQ ID NO: 6), VLDFAPPGA (SEQ ID NO: 7); NY-ESO1 peptide: SISSCLQQL (SEQ ID NO: 8), RLLEFYLAM (SEQ ID NO: 9), GVLLKEFTV (SEQ ID NO: 10), ILTIRLTAA (SEQ ID NO: 11); and MAGE-A3 peptide: LLIIVLAII (SEQ ID NO: 12), KIWEELSVL (SEQ ID NO: 13), LVFGIELMEV (SEQ ID NO: 14), SLPTTMNYPL (SEQ ID NO: 15).

Example 3. Pilot Production of T Cell Therapeutic Agent Specific for Autologous Cancer Antigen Through epitope screening, 3-4 types of peptides of epitopes for each autologous cancer antigen suitable for preparation of a T cell therapeutic agent were selected, and pilot production of a T cell therapeutic agent specific for hTERT, WT1, NY-ESO1, and MAGE-AC was performed by using the peptides. Production of a T cell therapeutic agent includes three steps, that is, a first proliferation of autologous anticancer T cells, isolation and mass culture.

(1) Proliferation of Autologous Cancer Antigen-Specific CD8 T Cells 50 ml of blood was collected from a cancer patient who has been proven to have one or more of epitope having the score of at least 3, through epitope screening.

1) Isolation of PBMCs from blood of a patient: 7 ml of blood was allowed to slowly flow a 15 ml comical tube filled with 7 ml of ficollhypaque such that the blood was overlaid on supernatant of the ficoll solution. The tube was centrifuged for 20 minutes at 2000 rpm at room temperature, and then only a cell layer, which is located between ficoll and plasma and has white color, was collected, washed, and used as PBMCs.

2) Isolated PBMCs were suspended in CTL medium (RPMI1640 medium+4 mM L-glutamine+12.5 mM HEPES+50 μM 2-mercaptoethanol+3% autoplasma) to become the concentration of $1\times10^6$ cells/ml, 3-4 types of peptides selected by epitope screening of the present invention were added such that the concentration of each peptide became 1 μg/ml. 1 ml of the cell suspension was aliquoted in a 14 ml round tube, and cultured in a $CO_2$ incubator.

3) Two days after culture, 1 ml of CTL medium including 50 U/ml IL-2 (Proleukin, Novatis) was added to each tube.

4) On day 7, 9, 11, and 13 of culture, 1 ml of the supernatant medium was removed, and CTL medium including 50 U/ml IL-2 was added.

5) After 14 days of culture, cells in each tube were collected in a 50 ml comical tube. Then, RPMI1640 medium was added, and the tube was then centrifuged for 5 minutes at 1400 rpm to wash cells. The process was repeated twice more.

6) The washed cells were suspended in CTL medium such that the concentration of cells became $2\times10^6$ cells/ml. Then, 3-4 types of the same peptides were added in the concentration of 5 μg/ml, respectively, and thereafter the resultant was cultured.

(2) Selection of Autologous Cancer Antigen-Specific CDS T Cells

1) After 24 hours of culture, PBMCs, which were reactivated for a day, were collected, and washed twice with RPMI1640 medium. Then, PBMCs were suspended in CTL medium such that the concentration of PBMCs became $5\times10^6$ cells/ml. Thereafter, 50 U/ml of IL-2 was added.

2) 1 ml of the cells were added to a 6-well or 12-well culture plate which was coated with an anti-4-1BB antibody in the concentration of 50 μg/ml for a day, and then the resultant was cultured for 10 minutes in a $CO_2$ incubator.

After 10 minutes of culture, washing was performed to remove all cells which were not attached to the plate. Then, 2 to 4 ml of CTL medium including 1000 U/ml IL-2 was added to each well, and the resultant was cultured for two days in a $CO_2$ incubator.

(3) Mass Culture of Autologous Cancer Antigen-Specific CD8 T Cells

1) Whole cells, which were isolated with the anti-4-1BB antibody and cultured for two days, were collected, washed with RPMI1640 medium twice and counted.

2) PBMCs were isolated from a healthy donor; suspend such that the concentration of PBMCs became $1\times10^8$ cells/ml; and irradiated with radiation of 3000 rad to induce cell death so that the resultant was used as a culture additive capable of providing costimulation which is needed to induce proliferation of T cells.

3) To a 50 ml comical tube, were added $5\times10^5$ cells of the isolated CD8 T cells and $1\times10^8$ cells of irradiated allogenic PBMCs. Then, ALyS505N medium (CELL SCIENCE & TECHNOLOGY INST., INC. (CSTI)) including 1,000 U/ml of IL-2, 40 ng/ml of an anti-CD3 mAb (BD Bioscience) and 3% of autoplasma was added q.s. to 50 ml.

4) 50 ml of cell suspension was injected in a 1 L culture bag and cultured in a $CO_2$ incubator.

5) After 4 days of culture, 50 ml of ALyS505N medium including 1,000 U/ml of IL-2, and 3% of autoplasma was additionally injected to the 1 L culture bag.

6) After 7 days of culture, 1 00 ml of ALyS505N medium including 1,000 U/ml of IL-2, and 3% of autoplasma was additionally injected to the 1 L culture bag.

7) After 9 days of culture, 300 ml of ALyS505N medium including 1,000 U/ml of IL-2, and 3% of autoplasma was additionally injected to the 1 L culture bag.

8) After 11 days of culture, 500 ml of ALyS505N medium including 1,000 U/ml of IL-2, and 3% of autoplasma was additionally injected to the 1 L culture bag.

9) After 14 days of culture, whole cells in the 1 L culture bag were collected, and washed with injectable physiological saline three times. Then, the cells were suspended in injectable physiological saline including 5% of albumin to fill a complete product of a T cell therapeutic agent.

As above, 3-4 types of peptides having a score of at least 3 which can induce T cell response were selected from a clinical cancer patient trough epitope screening of the present invention. The pilot production of hTERT, WT, NY-ESO1, and MAGE-A3 T cell therapeutic agents was performed by using 50 cc of blood. The results were summarized in FIGS. 6 to 9.

Figure 14:
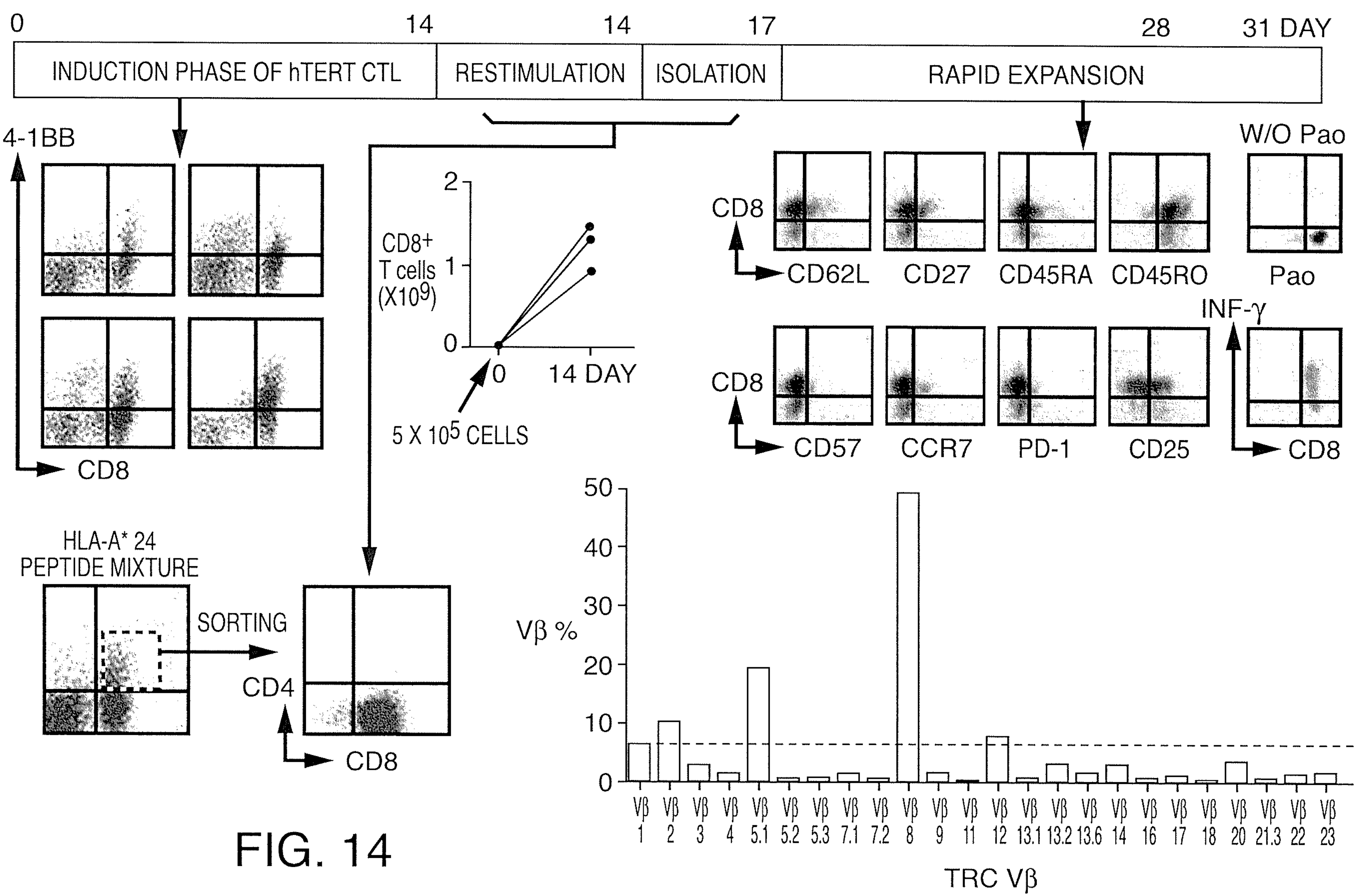
FIG. 14 illustrates a pilot production process of an hTERT T cell therapeutic agent.

FIG. 14 illustrates a process of pilot production of an hTERT T cell therapeutic agent.

In FIG. 14, PBMCs were isolated from 50 cc of blood of a gastric cancer patient having HLA-A*24 allele. Three types of hTERT peptides, i.e. CLKELVARV (SEQ ID NO: 1), PLFLELL (SEQ ID NO: 2), and AAVTPAA (SEQ ID NO: 3) were added in the concentration of 1 μg/ml for each. Then, the resultant was cultured according to the process described in "(1) proliferation of autologous cancer antigen-specific CD8 T cells" in Example 3 above. After 14 days of culture, whole cells were collected, and T cells, which reacted with the hTERT peptide, and were thus proliferated, were isolated/proliferated according to the process in "(2) selection of autologous cancer antigen-specific CD8 T cells". The isolated T cells were mass cultured to a level sufficient to be administered to a cancer patient through the process in "(3) mass culture of autologous cancer antigen-specific CD8 T cells". The cultured final cells were analyzed as particular TCRVb type T cells having low catabiosis and a working function through flow cytometry.

Figure 15:
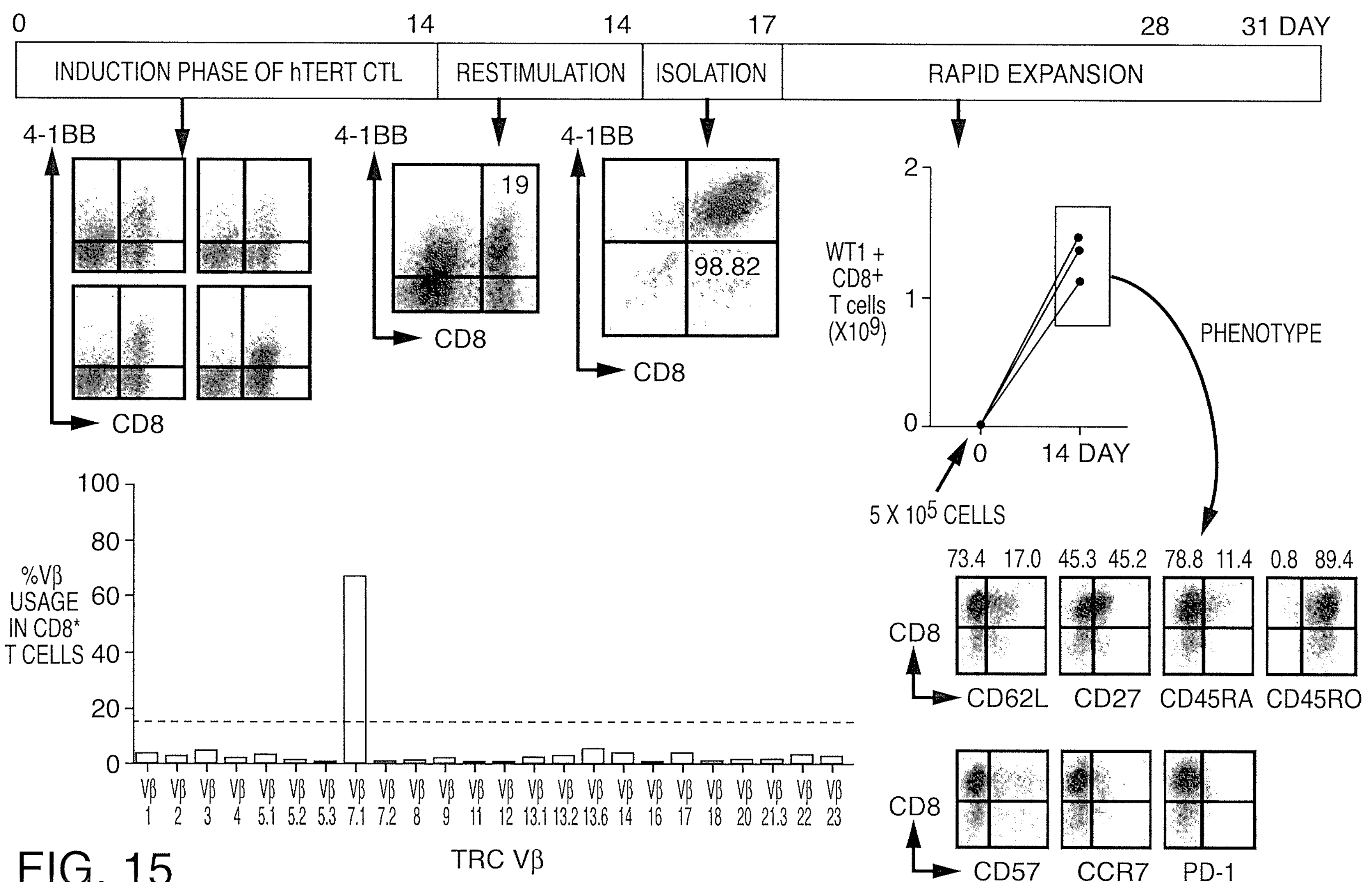
FIG. 15 illustrates a pilot production process of a WT1 T cell therapeutic agent.

FIG. 15 illustrates a process of pilot production of a WT1 T cell therapeutic agent.

In FIG. 15, PBMCs were isolated from 50 cc of blood of a malignant glioblastoma patient having HLA-A*24 allele. Four types of WT1 peptides, i.e., SLGEQQVSV (SEQ ID NO: 4), RMFPNAPVL (SEQ ID NO: 5), CMTWNQMNL (SEQ ID NO: 6), and VLDFAPPGA (SEQ ID NO: 7) were added in the concentration of 1 μg/ml for each. Then, the resultant was cultured according to the process described in "(1) proliferation of autologous cancer antigen-specific CD8 T cells" in Example 3 above. After 14 days of culture, whole cells were collected, and T cells, which reacted with the WT1 peptide, and were thus proliferated, were isolated/proliferated according to the process in "(2) selection of autologous cancer antigen-specific CDS T cells". The isolated T cells were mass cultured to a level sufficient to be administered to a cancer patient through the process in "(3) mass culture of autologous cancer antigen-specific CDS T cells". The cultured final cells were analyzed as particular TCRVb type T cells having low catabiosis and a working function through flow cytometry.

Figure 16:
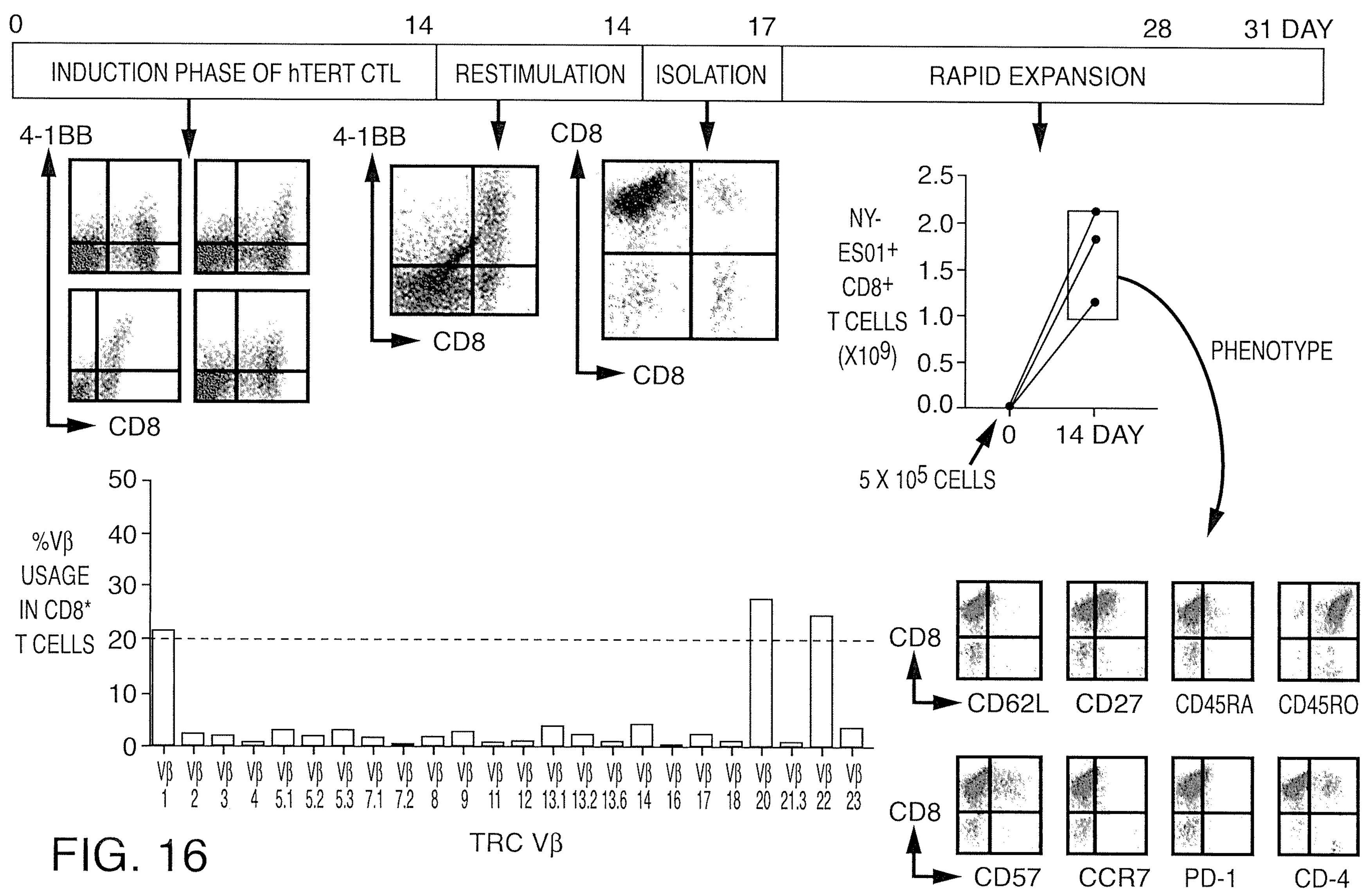
FIG. 16 illustrates a pilot production process of an NY-ESO1 T cell therapeutic agent.

FIG. 16 illustrates a process of pilot production of an NY-ESO1 T cell therapeutic agent.

In FIG. 16, PBMCs were isolated from 50 cc of blood of an ovarian cancer patient having HLA-A*02 allele. Four types of NY-ESO1 peptides, i.e. SISSCLQQL (SEQ ID NO: 8), RLLEFYLAM (SEQ ID NO: 9), GVLLKEFTV (SEQ ID NO: 10), and ILTIRLTAA (SEQ ID NO: 11) were added in the concentration of 1 μg/ml for each. Then, the resultant was cultured according to the process described in "(1) proliferation of autologous cancer antigen-specific CD8 T cells" in Example 3 above. After 14 days of culture, whole cells were collected, and T cells, which reacted with the NY-ESO-1 peptide and were thus proliferated, were isolated/proliferated according to the process in "(2) selection of autologous cancer antigen-specific CDS T cells". The isolated T cells were mass cultured to a level sufficient to be administered to a cancer patient through the process in "(3) mass culture of autologous cancer antigen specific CDS T cells". The cultured final cells were analyzed as a particular TCRVb type T cells having low catabiosis and a working function through flow cytometry.

Figure 17:
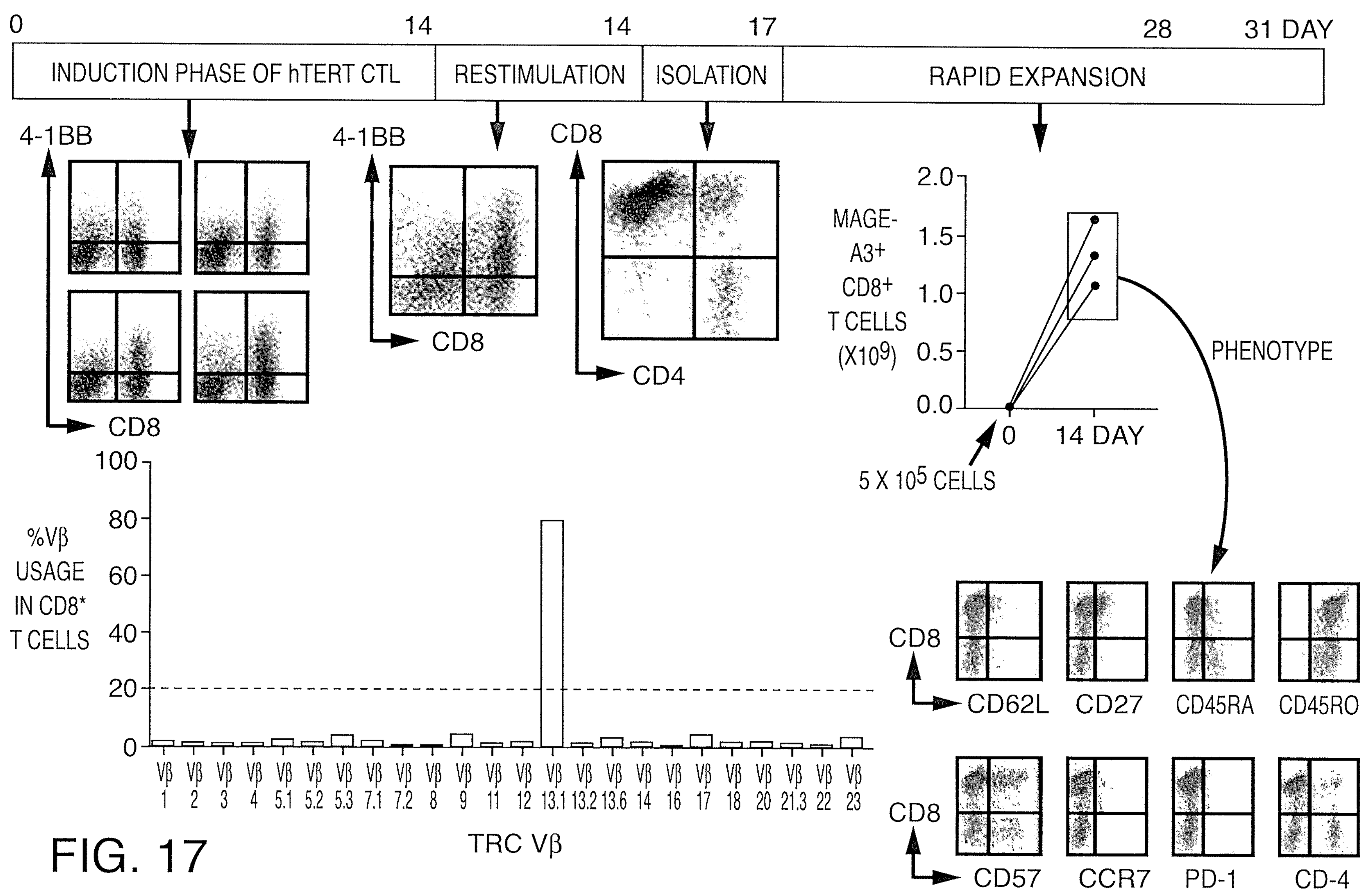
FIG. 17 illustrates a pilot production process of an MAGE-A3 T cell therapeutic agent.

FIG. 17 illustrates a process of pilot production of an MAGE-A3 T cell therapeutic agent.

In FIG. 17, PBMCs were isolated from 50 cc of blood of a sarcoma patient having HLA-A*02 allele. Four types of MAGE-A3 peptides, i.e. LLIIVLAII (SEQ ID NO: 12), KIWEELSVL (SEQ ID NO: 13), LVFGIELMEV (SEQ ID NO: 14), and SLPTTMNYPL (SEQ ID NO: 15)] were added in the concentration of 1 μg/ml for each. Then, the resultant was cultured according to the process described in "(1) proliferation of autologous cancer antigen-specific CD8 T cells" in Example 3 above. After 14 days of culture, whole cells were collected, and T cells, which reacted with the MAGE-A3 peptide were thus proliferated, were isolated/proliferated according to the process in "(2) selection of autologous cancer antigen-specific CD8 T cells". The isolated T cells were mass cultured to a level sufficient to be administered to a cancer patient through the process in "(3) mass culture of autologous cancer antigen specific CD8 T cells". The cultured final cells were analyzed as a particular TCRVb type T cells having low catabiosis and a working function through flow cytometry.

Hereto, the present invention is described referring to preferred examples thereof. A person with ordinary skill in the art to which the present invention pertain would understand that the present invention could be implemented in various aspects different from each other without departing from the essential feature of the present invention. Therefore, the disclosed examples are to be construed as being illustrative, and not restrictive. The scope of the present invention is to be determined by the appended claims, not detailed description above, and all modifications fallen within the equivalent range should be interpreted to be included in the present invention.

What is claimed is:

1. A method for isolating autologous cancer antigen-specific CD8+T cells, the method comprising a) culturing peripheral blood mononuclear cells (PBMCs) isolated from blood of a cancer patient in a cell culture medium with three or more peptides, and I1-2, wherein
   (i) the cancer patient has a HLA-A*024 allele and an autologous cancer antigen of hTERT, and the three or more peptides comprise SEQ ID NO:1-3;
   (ii) the cancer patient has a HLA-A*024 allele and an autologous cancer antigen of WT1, and the three or more peptides are selected from a group consisting of SEQ ID NO: 4-7;
   (iii) the cancer patient has a HLA-A*02 allele and an autologous cancer antigen of NY-ESO1, and the three or more peptides are selected from a group consisting of SEQ ID NO: 8-11;
   (iv) the cancer patient has a HLA-A*02 allele and an autologous cancer antigen of MAGE-A3, and the three or more peptides are selected from a group consisting of SEQ ID NO:12-15; and wherein culturing the PBMCs with the three or more peptides induces 4-1BB expression;

b) selecting cultured cells using an anti-4-1BB antibody, thereby isolating autologous cancer antigen-specific CD8+ T cells.

2. The method of claim 1, wherein autologous cancer antigen-specific $CD8^+$ T cells are less than 0.1% of all T cells present in blood of the cancer patient.

3. The method of claim 1, wherein the cell culture medium in step a) comprises plasma that is autologous to the cancer patient.

4. The method of claim 1, wherein the culturing step a) is performed for 12 to 16 days.

5. The method of claim 1 wherein expression of 4-1BB is induced by culturing the cells of step a) for 12-36 hours.

6. The method of claim 1, wherein the selecting step b) comprises culturing cells in which 4-1BB expression is induced on a culture plate coated with an anti-4-1BB antibody.

7. The method of claim 6, wherein the selecting step b) is performed for 1 to 20 minutes.

8. The method of claim 1, wherein the autologous cancer antigen in step a) is hTERT.

9. The method of claim 1, wherein the autologous cancer antigen in step a) is NY-ESO1.

10. The method of claim 1, wherein the autologous cancer antigen in step a) is MAGE-A3.

11. The method of claim 1, wherein the autologous cancer antigen is step a) is WT1.

12. A pharmaceutical composition comprising autologous cancer antigen-specific $CD8^+$ T cells isolated by the method of claim 1 and a pharmaceutically acceptable carrier.

13. A method for treating cancer in a patient in need thereof comprising administering to the patient the pharmaceutical composition of claim 12, wherein (i) the cancer patient has a HLA-A*024 allele and an autologous cancer antigen of hTERT or WT1, or (ii) the cancer patient has a HLA-A*02 allele and an autologous cancer antigen of NY-ESO1 or MAGE-A3.

14. The method of claim 13, wherein the cancer is a solid tumor.

15. The method of claim 13, wherein the cancer is selected from lung cancer, gastric cancer, pancreatic cancer, melanoma, gliobastoma, leukemia, ovarian cancer, brain cancer, spinal cancer, germ cell cancer, breast cancer, and sarcoma.

* * * * *

UNITED STATES PATENT AND TRADEMARK OFFICE

CERTIFICATE OF CORRECTION

PATENT NO. : 10,570,371 B2
APPLICATION NO. : 15/936209
DATED : February 25, 2020
INVENTOR(S) : Byoung S. Kwon et al.

It is certified that error appears in the above-identified patent and that said Letters Patent is hereby corrected as shown below:

On the Title Page

Item [54], Column 1, Line 3, delete "CD8+T" and insert -- $CD8^+$ T --.

Item [57], Column 2, Line 10, delete "CD8 T" and insert -- $CD8^+$ T --.

In the Specification

Column 1, Line 3, delete "CD8+T" and insert -- $CD8^+$ T --.

In the Claims

Column 62, Line 42, Claim 15, delete "gliobastoma," and insert -- glioblastoma, --.

Signed and Sealed this
Twenty-seventh Day of October, 2020

Andrei Iancu
*Director of the United States Patent and Trademark Office*